United States Patent
Riverón Rojas et al.

(10) Patent No.: US 7,189,316 B2
(45) Date of Patent: Mar. 13, 2007

(54) PULSED FIELD ELECTROPHORESIS CHAMBERS, ACCESSORIES AND METHOD OF UTILIZATION FOR SEPARATION OF DNA MOLECULES

(75) Inventors: Ana Maria Riverón Rojas, Cuidad de Habana (CU); Lilia López Cánova, Cuidad de Habana (CU); Oscar Arencibia Díaz, Cuidad de Habana (CU); Jose Alfredo Herrera Isidrón, Cuidad de Habana (CU); Gabriel Pérez Pérez, Cuidad de Habana (CU); Esther Orozco Orozco, Mexico City (MX); Carlos Alberto Cánino Ramos, Cuidad de Habana (CU); Luis Mariano Batista Santiler, Cuidad de Habana (CU); Regnar Gigato Pérez, Cuidad de Habana (CU); Leonardo Ruíz Esquivel, Cuidad de Habana (CU); Maria Dolores Noa Blanco, Cuidad de Habana (CU); Elisa Javert Higginson, Cuidad de Habana (CU)

(73) Assignee: Centro Nacional de Investigaciones Cientificas, Havana (CU)

( * ) Notice: Subject to any disclaimer, the term of this patent is extended or adjusted under 35 U.S.C. 154(b) by 267 days.

(21) Appl. No.: 10/070,878

(22) PCT Filed: Jun. 7, 2001

(86) PCT No.: PCT/CU01/00003

§ 371 (c)(1),
(2), (4) Date: Aug. 19, 2002

(87) PCT Pub. No.: WO01/94932

PCT Pub. Date: Dec. 13, 2001

(65) Prior Publication Data

US 2003/0089607 A1    May 15, 2003

(30) Foreign Application Priority Data

Jun. 7, 2000    (CU) ................... 0135/00
Dec. 27, 2000  (CU) ................... 0306/00

(51) Int. Cl.
    *G01N 27/447* (2006.01)
(52) U.S. Cl. ............ 204/608; 204/618; 204/457; 204/467
(58) Field of Classification Search ........ 204/458, 204/609, 457, 467, 608, 618
    See application file for complete search history.

(56) References Cited

U.S. PATENT DOCUMENTS

| | | | | |
|---|---|---|---|---|
| 4,473,452 A | * | 9/1984 | Cantor et al. | 204/458 |
| 4,740,283 A | | 4/1988 | Laas et al. | |
| 5,011,586 A | * | 4/1991 | Finney et al. | 204/466 |
| 5,084,157 A | | 1/1992 | Clark et al. | |
| 5,165,898 A | | 11/1992 | Chu et al. | |
| 6,063,250 A | | 5/2000 | Becker | |

FOREIGN PATENT DOCUMENTS

| | | |
|---|---|---|
| EP | 0 745 844 A2 | 12/1996 |
| GB | 2 249 395 A | 5/1992 |
| WO | WO 01/07150 A2 | 2/2001 |

OTHER PUBLICATIONS

Riveron, A. M. et al, "Fast Pulsed Field Minigel Electrophoresis of Large DNA Molecules", Anal. Lett. 28, 1973-1991. (1995).*

* cited by examiner

*Primary Examiner*—Nam Nguyen
*Assistant Examiner*—Jeffrey Barton
(74) *Attorney, Agent, or Firm*—Lackenbach Siegel, LLP

(57) ABSTRACT

Methods of use, accessories and chambers, optimal for performing Pulsed Field Gel Electrophoresis (PFGE) of DNA molecules in 'Contour Clamped Homogeneous Electric Field' (CHEF) and 'Transversal Alternating Field Electrophoresis' (TAFE) systems, are provided herein. DNA molecules are rapidly separated in the minigels of these chambers. The sizes of chambers and accessories are determined by the separation between the opposite polarity electrodes; which is comprised between 6.2 and 15 cm. Reproducibility of molecule separation is achieved because the accessories warrant homogeneous electric resistance in the buffer and minigels. Chambers allow a high-throughput sample format using the reagents efficiently. It is attained excluding the non-useful electrophoresis zones For a better optimization, TAFE chambers have several useful electrophoresis zones (UEZ), each carrying a minigel. One or more UEZ can be activated at will in the electrophoresis, to vary the number of minigels, the number of samples and the amount of buffer among the experiments. TAFE chambers having 'inverted electrode configuration' with the cathodes at their bottom are presented.

26 Claims, 18 Drawing Sheets

PULSED FIELD ELECTROPHORESIS CHAMBERS, ACCESSORIES AND METHOD OF UTILIZATION FOR SEPARATION OF DNA MOLECULES

CLAIMS OF PRIORITY

This application claims priority to Cuban Application Nos. CU 0135/00 filed Jun. 7, 2000, CU 0306/00, filed Dec. 27, 2000 and PCT/CU01/00003, filed Jun. 7, 2001.

REFERENCE TO RELATED APPLICATION

The present invention is related to the field of Molecular Biology and more particularly, it refers to Pulsed Field Gel Electrophoresis chambers of the 'Contour Clamped Homogeneous Electric Field' (CHEF) and 'Transversal Alternating Field Electrophoresis' (TAFE) systems. This invention is also related to the use of these chambers for the separation of DNA molecules and a method for the selection of the conditions of electrophoresis.

BACKGROUND OF THE INVENTION

Pulsed field gel electrophoresis (PFGE) dates from 1984, when Schwartz D. C and Cantor C. (Cell, 37, 67–75, 1984; U.S. Pat. No. 4,473,452) observed that applying electric pulses that periodically alternated their direction in a certain angle in relation to an agarose gel, large intact DNA molecules were resolved as band patterns. The authors also determined that the separations of the molecules essentially depended on the duration of the electric pulses. Later, it was determined that the geometry of the lines of force of the approximates alternating electrical fields, the strength of them, the experimental temperature, the ionic strength of the buffer solution and the concentration of the agarose gel were important factors that influenced the resolution that could be achieved among DNA molecules. (Birren B. and Lai E. Academic Press. New York, 1993, p 107, 111, 129, 131, 135; López-Cánovas L. et al., J. of Chromatogr. A, 1998, 806, 123–139; López-Cánovas L. et al., J. of Chromatogr. A, 1998, 806, 187–197).

Pulsed field electrophoresis renders the separation of the DNA molecules as band patterns Each pattern is formed in the lanes of the separation gels after the electrophoresis. Altogether, the agarose plugs containing the immobilized DNA molecules are loaded into each well of the gel, then, the molecules migrate along the length of the gel and form the band patterns during the electrophoresis. That is why this type of electrophoresis has associated a method for the preparation of intact DNA molecules immobilized in plugs of gel. These molecules can be or not, digested with restriction endonucleases before the electrophoresis.

Several systems to perform PFGE have been developed. They are characterized for having chambers in which the electrodes are placed in different arrangements Among these chambers are the OFAGE (Orthogonal Field Alternating Gel Electrophoresis, Carle C. F. and Olson M. V. Nucleic Acids Res. 1984, 12, 5647–5664) CHEF ('Contour Clamped Homogeneous Electric Field', Chu G. Science 234, 1986, 1582–1585), TAFE ('Transversal Alternating Field Electrophoresis', U.S. Pat. No. 4,740,283), FIGE ('Field Inversion Gel Electrophoresis', U.S. Pat. No. 4,737,251 of Carle G. F. and Olson M. V) arrangement of electrodes, and the minichambers MiniTAFE and MiniCHEF (Riverón, A. M. et al., Anal. Lett, 1995, 28, 1973–1991; European Patent Application EP 0 745 844).

All these systems are characterized by having electronic circuitry for alternating the electric fields and accessories for the preparation of the gel. There are also accessories for the preparation of the samples. The systems differ among them by the complexity of the electronics to energize the electrodes and to switch the orientation of the electric field They also differ by their capacity to render straight paths of migration of the band patterns The possibility to obtain straight paths of migration is essential when the comparison of the patterns of several samples is wished, while the simplicity of the electronics facilitates and makes cheaper the construction of the systems. Among the systems mentioned, only three render straight paths of migration of the molecules:

1.—the CHEF system, which has electrodes that are clamped to predetermined electrical potentials, electrodes that are arranged in a hexagonal contour around a submarine gel that is horizontally positioned;
2.—the TAFE system, in which the electrophoresis is performed in submarine gels that are positioned vertically in the chamber and uses fields transversal to the surfaces of the gel; and
3.—the FIGE system, in which the electrophoresis is performed in horizontal submarine gels that are positioned in conventional electrophoresis chambers, which have two electrodes. In this system, the orientation of the electric field is reverted periodically These systems have in common that in their chambers the gel is symmetrically crossed by the lines of force of the electric fields that are generated at the electrodes with opposite polarity in the electrode arrangement. In that gel, the samples containing the intact DNA molecules are loaded. In all these chambers exist zones where the force lines of the electric field do not act on the molecules. The zone of the chamber that contains the gel and is crossed by the lines of force of the electric field that directly interact with the molecules will be denominated here as useful electrophoresis zone (UEZ) Whereas the zones of the chamber crossed by the lines of force of the electric field that do no act on the molecules will be denominated here as non-useful electrophoresis zones (NEZ) All existing chambers to perform PFGE have a single UEZ and several NEZ regions The chamber and the electronics of the FIGE system are simple. FIGE chambers that allow the simultaneous analysis of many samples exist (up to 96 samples, using two combs of 48 teeth in the chamber OnePhorAll Submarine Gel System of Jordan Scientific, BDH Catalogue BDH, 1997, Section E p 4–371), but in these chambers inversion of the mobility of the molecules occur (Carle G. F., Frank M. and Olson M. V. Science, vol. 232, p 65–68, 1986). Due to the absence of a theory that predicts the inversion mobility in FIGE under any experimental conditions, such inversion limits the use of these chambers to analyze the size of DNA molecules separated and to compare their band patterns. For instance, this phenomenon will cause that two DNA molecules of different sizes migrate the same distance in the gel, preventing their identification, excepting by means of hybridization with DNA probes. Up to now, the two only ways to estimate the size of large DNA molecules separated in experiments of PFGE are 1) To compare the distances migrated by the molecules under study to the distances migrated by the size markers and
2) To use equations that describes the distances migrated by the molecules under different electrophoresis conditions and later replace in the equations the migrated distances and the experimental variables.

In FIGE the size markers can also suffer mobility inversion and, as mentioned above, there is no theory capable to predict the moment and conditions of appearance of such inversion. These are serious drawbacks of FIGE chambers, especially to compare many samples, for instance, in molecular epidemiology studies. Because of these reasons the systems most frequently used to compare band patterns of many samples are CHEF and TAFE.

Gardiner K. et al. in their paper published in Somatic Cell Mol. Genet. 1986, 12, 185–195 proposed the TAFE system. They called it "Vertical Pulsed Field Electrophoresis" (VPFE) and developed an equipment which was disclosed in U.S. Pat. No. 4,740,283 dated Apr. 26 of 1988. This system for the separation of DNA molecules uses a vertical gel of 10×7.6×0.6 cm (height×width×depth) and has the electrodes arranged in parallel to the faces of the gel and across the chamber. In the chamber, each member of a pair of electrodes with opposite polarity is positioned in front of a face of the gel. The cathode is positioned at the top and near the origin of migration and the anode far from it, at the bottom. Such electrode arrangement generates equipotential lines spanning the length of the gel and a gradient potential or electric field, where the lines of force of such electric field cross the gel transversally. Then, along the height of the gel a gradient of electric field strength and of the angle formed between the lines of force of the two pair of electrodes are obtained. That is the reason why the molecules are compelled to migrate during each pulse through the thickness of the gel. The resultant migration occurs in vertical direction, downward. Despite of the existence of these gradients, all the gel points situated widthwise and at the same height, in relation to the plane that contains both cathodes or both anodes, are at a same value of electric potential (equipotential lines) Thus, molecules of the same size migrate similar distances during the electrophoresis in all the lanes of the gel and migrate following straight paths up to the same height in the gel, independently on the wells in which the samples were loaded.

Based on these principles, Beckman Instrument, Inc. (Beckman, The Geneline System Instruction Manual, ed. Spinco Division of Beckman Instruments, 1988), constructed the equipment called "Geneline I", or "Transverse Alternating Field Electrophoresis System" known as TAFE. This system uses a gel of 11×7.2×0.6 cm (height×width× thickness), which is placed between the pairs with opposite electrodes that are separated 20 cm. Later, Beckman Instruments, Inc. developed the equipment "Geneline II" in which the gel was enlarged to 14.2×15×0.3 cm. The Geneline II equipment is no longer been produced.

To resolve large DNA molecules in a band pattern, a long time is required in the TAFE equipments Geneline I and Geneline II. For instance, Geneline I needs 24 hours to render a pattern of 11 bands corresponding to the chromosomes of the yeast *Saccharomyces cerevisiae* (molecules less than 1.6 Mb in length. 1 Mb=$10^6$ base pairs). This equipment may heed up to 90 hours to separate the DNA molecules of the amoebic genome in 17 bands (Orozco E. et al., Molec. Biochem. Parasitol. vol. 59, p 29–40, 1993) TAFE chambers require a large volume buffer solution to cover the electrodes (approximately 3500 ml in Geneline II) and through the electrophoresis buffer the flow of electric current is high and the generated heat might be large. If in the TAFE equipment, the potential difference applied across the electrodes with opposite polarity is increased, the maximum current output of the power supply may be achieved. That is why, the companies recommend 10 V/cm as the maximum value of electric field (for power supplies with a maximum current output of 0.4 Amp). Large heat generation in the electrophoresis impedes the reduction of the duration of electrophoresis by increasing the electric field strength. It has been stated that the use of elevated voltages or high temperatures broaden and make diffuse the bands of the electrophoresis pattern, rendering poorly resolved bands. The advantage of the Geneline II is to permit the simultaneous analysis of 40 samples, which facilitates the comparative analysis of the electrophoresis patterns given by many samples.

Gilbert Chu (Science 1986, 234, 16, 1582–1585) developed CHEF system on the following basis: a homogeneous electric field is theoretically generated by two infinite electrodes placed in parallel at certain distance. To simulate a homogeneous field using finite electrodes, another group of electrodes is placed in a plane, along a closed polygon, that might be a square or a hexagon.

The x axis (y=0) of the plane is set to coincide with a side of the polygon and zero volt is applied. The opposite side is placed at a distance 'A' (y=A) from the origin of ordinates and it is polarized to a potential 'Vo'. The rest of electrodes are polarized according to $V(y)=Vo \cdot y/A$. In this way, the potential generated in the interior of the polygon is equal to those that should be generated by two infinite parallel electrodes separated a distance 'A' The reorientation angle obtained by electronic permutation of the polarity between two pairs of different sides will be 90° for the square and 60° or 120° for the hexagon A method to clamp the desired potentials across the CHEF electrodes is to set a series of resistors wired to form a voltage divisor between potentials $V(0)=0$ and $V(A)=Vo$ From each of the nodes, formed by the union of two resistors, the voltage for the polarization of one electrode is withdrawn.

Based in these principles, the Bio-Rad Company developed the equipments CHEF-DR II, CHEF-DR III and CHEF Mapper (U.S. Pat. No. 4,878,008, U.S. Pat. No. 5,084,157 and U.S. Pat. No. 5,549,796). The last is the most advanced system. To clamp the voltages across the electrodes of the hexagonal array, the voltage divisor is wired to a transistorized system and operational amplifiers. This electronic design warrants that the voltages that are applied across the electrodes of the hexagonal array will be always correct.

The dimensions of the CHEF Mapper electrophoresis chamber are 11.4×44.2×50.3 cm (height×width×depth), it weights 10.2 Kg and uses 2.2 liters of buffer solution. This system uses a gel of 14×13 cm (width and length) that is concentrically positioned with the hexagonal arrangement of 24 electrodes, whose parallel sides are separated 30 cm or more. CHEF Mapper is also capable to use a wider gel where up to 40 samples can be loaded into.

The TAFE and CHEF equipments are able to separate chromosomal sized DNA molecules. Nevertheless, a common disadvantage of the CHEF and TAFE equipments is that the chambers are unnecessarily large, because their dimensions have not been optimized yet, particularly when thin sample plugs are used. It has been demonstrated that the thickness of the agarose plugs that contain the DNA samples influences the resolution of the bands, the electrophoresis time and the length of the gel to be used (López-Cánovas L. et al. J Chromatogr. A, 1998, 806, 187–197). In that work, it was demonstrated that if it is wished to obtain a resolution 'X' between two any molecules, this value is obtained in less space and less time if the bands are thinner, which is achieved if the plugs are also thinner. Among the consequences of using large electrophoresis chambers are:

I) When high electric fields are applied, the use of power supplies with large maximum output is required. These chambers have more than 20 cm of distance between the electrodes with opposite polarity; therefore, the maximal electric field that can be applied in these equipments is approximately 10 V/cm.

II) The experiments are long in these chambers. Two factors influence long run duration, very low electric fields are used (usually 6 V/cm), and samples are around 0.1 cm thickness. For instance, normal experiments take 24 hours to obtain the electrophoresis patterns of the eleven chromosomal bands, corresponding to DNA molecules of Saccharomyces cerevisiae less than 1.6 megabases ($10^6$ base pairs), and up to 90 hours to separate the 17 bands of DNA molecules from the genome of *Entamoeba histolytica* (Orozco E et al, Mol. Biochem. Parasitol. 1993, 59, 29–40).

III) The equipments are not economical, because large amount of expensive reagents (such as Tris and agarose) and biological samples are used. The latter might impede certain applications (for instance in clinical diagnosis).

IV) A large quantity of heat is generated in the electrophoresis chamber when the driving force of the electrophoresis or electric field (which depends on the applied voltage across the electrodes and on the current intensity that flows through the buffer solution) is increased. If the electric field is increased (aimed to increasing the velocity of separation), it should be done by increasing the voltage applied across the electrodes, and therefore the current intensity By Joule effect, the generation of heat in the chamber will increase. An excessive increase of heat evolved will broaden and make the bands diffuse and will provoke distortion of the electrophoresis pattern and even entrapment of DNA molecules in the pores of the gel and the complete absence of migration.

Nevertheless, the large volume of buffer solution filling these chambers has the advantage that the turbulences generated in the solution during its circulation are attenuated. Altogether, the gel is so distant from the electrodes that any local change in conductivity near the electrodes produced by electrolysis is diluted and will not have deleterious effect due to the large volume of solution.

In 1995 were disclosed the MiniCHEF and MiniTAFE equipments, in which Pulsed Field Gel Electrophoresis of 8 samples loaded into a gel are performed (Riverón A. M. et al., Anal. Lett, 1995, 28, 1973–1991; European Patent Application EP 0 745 844) These equipments overcame the deficiencies of the above-mentioned systems. The MiniCHEF as well as the MiniTAFE use thin samples thinner than 0.1 cm and they allow the application of higher electric fields rendering adequate resolutions among the bands of the patterns. Therefore, in the miniequipments, the chromosomes of the yeast *Saccharomyces cerevisiae* were resolved in 4 to 5 hours.

The separation between the opposite electrodes of minichambers is small, thus allowing the construction of smaller chambers and the use of less volume of buffer to cover the electrodes and the gel (Riverón A. M. et al., Anal. Lett, 1995, 28, 1973–1991; European Patent Application EP 0 745 844, Bull. 1996/49). That is why in MiniCHEF and MiniTAFE, low amount of heat is not evolved, even if high electric fields are applied The samples loaded into the gels of these equipments need a small amount biological material (Riverón A. M. et al., Anal. Lett, 1995, 28, 1973–1991). Furthermore, they save laboratory bench space.

The authors of these equipments demonstrated the feasibility of performing PFGE in gels that are not long. For instance, gels of 4 cm in length were used. By means of the use of mini-equipments López-Cánovas L. et al. (López-Cánovas L. et al., J Chromatogr A, 1998, 806, 187–197) demonstrated that plugs thicker than 0.1 cm render thick bands and the molecules need more time and more gel length to be separated. In addition, the use of thick samples does not improve the quality of the electrophoresis pattern and does not reveal more bands.

The mini-equipments proposed by Riverón A. M. et al. to perform Pulsed Field Gel Electrophoresis have chambers whose sizes are calculated based on the existence of other equipments of larger dimensions (Riverón A. M. et al., Anal. Lett, 1995, 28, 1973–1991; European Patent Application EP 0 745 844). Therefore, they can inherit errors of the equipments from which they were designed. In fact, the mini-equipments inherited from the large chambers an open system for the preparation of the gel and the absence of a proper system for attenuating turbulences of the buffer flowing throughout the chamber In the patent application and the related papers, the effects of the reduction of the volumes of the buffer and the gel on the electrophoresis pattern are not mentioned That is, the question whether this volume of buffer is enough to attenuate the turbulences during its circulation, or whether the irregularities in the gel and the differences in dimensions of the plugs influence the quality of the bands patterns that are obtained, are not resolved yet These troubles increase with miniaturization, because miniaturization magnifies the manufacture errors. For instance, if a meniscus of 0.1 cm height is formed in a gel of 1 cm of thickness, the error in the height of the gel would be 10%, while that same error in a 0 4 cm thick gel represents 25%. Therefore, the magnification of the errors by miniaturizing the system can become critical factors to obtain reproducible bands patterns The relevant parameter of pulsed field electrophoresis equipments is the separation between the electrodes, because it determines the values of electric field that can be applied. It also determines the driving force of the molecules, the dimensions of the chambers, the systems that should be used to homogenize the variables of the electrophoresis, the length of the separation gel, the thickness of the plugs where the samples are included and the width of each sample If the separation between the electrodes with opposite polarity is not optimal, for instance, if it is too large, then the dimensions of the gel, the chamber and the number of samples that can be applied in those gels will not be optimal. If the plugs do not have the proper thickness and size, an excessive quantity of gel will be used and large electrophoresis time will be consumed. In addition, the shape and distribution of the dimensions of the chambers as well as the existence of a single UEZ region determines that the reagents consumed in these chambers will not be used optimally. Therefore, the desired goal is to develop chambers with optimal dimensions, which allow the application of high electric fields; chambers whose internal dimensions vary according to the number of samples they analyze and that the electrophoresis run time to be short without loosing resolution or high capacity of sample analysis.

From the above reasons, it is concluded that.

Large chambers of the current PFGE systems are not optimal, because the separation between electrodes with opposite polarity is unnecessary large and the same amount of reagents is used, independently on the number of samples to be studied.

The chamber dimensions are not optimal. The dimensions of the chambers (height, width and depth) do not warrant that the current flowing through the chamber does not exceed easily the output limits of the power supplies for PFGE, and thus, and do not separate the molecules fast at high electric fields.

In order to increase the number of UEZ, relevant constructive modifications have to be carried out in the existing chambers. They may affect the proper functioning of the systems. This factor influences the optimization of the use of reagents.

As it was already mentioned, the TAFE chambers (Geneline I, Geneline II) and MiniTAFE have an electrode platform to accommodate a gel (or two gels in Geneline II) Electrode platform whose width is equal to the width of the chamber and its height depends on the separation between the electrodes with opposite polarity (that is, they have an UEZ region). In the gel(s), so samples can be applied as many as is allowed by its width, the width of the samples and the separation between them. The equipments that have an UEZ region use a constant volume of buffer solution to cover its electrodes.

If the number of samples that is desired to be simultaneously analyzed exceed the maximal capacity of analysis of the UEZ of any of the mentioned chambers (for instance, more than 8 in MiniTAFE, more than 20 in Geneline I and more than 40 in Geneline II), it would be necessary to perform several electrophoresis. Therefore, the comparison of the resulting band patterns will not be reliable. For instance, when it is desired to characterize the genome of 100 isolates of a particular microorganism, either from a collection of isolates of the biotechnological industry, or infected human, animal or vegetables Then, these three chambers have insufficiencies in their capacity to simultaneously analyze more than 8, 20 or 40 samples, respectively, or are insufficient the possibilities to increase the capacity of analysis. Therefore, when it is necessary to perform co-electrophoresis of many samples to compare the band patterns of the DNA molecules of the samples the maximal capacity analysis of TAFE (Geneline I, Geneline II) and MiniTAFE can be exceeded.

A known solution, that would increase twofold the capacity of sample analysis of the mentioned chambers, is the implemented in the FIGE chamber OnePhorAll. This consists in positioning two combs in the gel of the UEZ, one of them at the beginning of the gel and the other in the middle of it. However, in the TAFE system, the samples loaded into the wells formed by the two combs would not be subjected to the same electric field nor to identical reorientation angle; thus molecules of similar size would migrate different distances in the gel and the bands patterns would not be comparable.

Another possible solution could be to construct wider chambers with wider gels and UEZ zones. This solution was implemented in Geneline II and supposedly; it should allow the analysis of many samples (more than 40). That is why Geneline II was designed as a non-deep but wide and tall chamber. However, it was necessary to place dielectrics between the electrodes and the gel in order to obtain the characteristic angle gradient of TAFE system. These dielectrics considerable slow down the electrophoresis runs. On the other side, the electric current flowing through the chamber depends directly on the cross section area that encounters the ionic flux. Thus, through these very tall and wide chambers flow elevated current, exceeding those flowing in Geneline I and the former VPFE. Therefore, by applying low voltages, the maximum current (Imax), or power (Pmax) outputs of the power supply, are reached in less time. For instance, Macrodrive I, LKB: Imax=0.4 Amp, Vmax=500 volts, Pmax=200 Watts; PowerPack 3000, Bio-Rad, Cat. 1998–1999: Imax=0.4 Amp, Vmax=3000 volts, Pmax=400 Watts; Consort E802, Cat. BDH 1997: Imax=2 Amp, Vmax=300 volts, Pmax=300 Watts (Vmax, Imax and Pmax maximum voltage, current and power outputs, respectively). Then, in this type of chambers is impossible to increase the electric field strength to reduce the electrophoresis time Low electric fields unnecessary enlarge the duration of PFGE experiments, fact that reduces the spectrum of applications of these chambers in the fields of the science and technology that require the rapid obtainment of results. In addition, Geneline II uses larger volume of reagents than current chambers. In fact, Beckman Instruments has discontinued Geneline II.

Wider miniTAFE chambers could be designed (maximum applicable electric field 25 V/cm for approximately 6 cm in width), because the chambers are neither deep nor tall The cross section area of miniTAFE could be increased if the electric current (I) flowing through the buffer at a given 'E' value (for instance 8–10 V/cm) does not exceed the maximum output of the existing power supplies. These chambers use less volume of buffer solution than the current TAFE, Geneline I and Geneline II chambers. In miniTAFE, the band patterns would be obtained in a relative short time However, such broad UEZ would need a very wide minigel, which would present difficulties in its casting and handling. Additionally, several minigels could be accommodated, but according to formula I (see forward), this chamber would not be efficient when analyzing a small number of samples. When it is necessary to analyze a small number of samples, for instance 8, the analyzing capacity of the gels of the TAFE Geneline I and Geneline II is largely wasted, because they have a single UEZ that can accommodate 20 or 40 samples, respectively The reagents used in PFGE experiments are expensive. The equipments would efficiently use their capacities of separation of DNA molecules if the volumes of reagents used each time in the chambers would depend on the number of samples to be analyzed. This is impossible in chambers of a single UEZ because they use a constant volume of reagents. The volume of reagents in excess (ER %) that is used in chambers of a single UEZ can be defined as $$ER(\%) = 100.0 \cdot (Nt-N)/Nt \qquad (I)$$

where:

Nt: Maximal number of samples that can be loaded in a minigel

N: Number of samples really analyzed in an experiment (Nt−N): Number of samples not loaded in the gel The ER values of the Geneline II and MiniTAFE systems are shown in Table 1 When few samples are analyzed, ER increases in both chambers, evidencing that they use reagents in excess when few samples are applied. Although miniTAFE (data in column 2 Table 1) uses less volume of reagents than TAFE, this volume neither varies with the number of samples analyzed. Hence, the volume of reagents used by the TAFE Geneline I, Geneline II and MiniTAFE chambers is constant and independent on the number of samples to be analyzed, fact that impedes its optimal use.

In addition, the buffer solution becomes exhausted during electrophoresis. That is why, to make an optimal design of the shape and dimensions of the chambers, it is necessary to know the time that the buffer solution takes to exhaust.

The chambers of the TAFE system to separate DNA molecules use a vertically placed gel and its cathodes are located at the top of the chamber. Then, the direction of migration is parallel to the vector of the gravity force. To avoid accidents with the electrodes while placing the gel in the chamber, Geneline I have two removable electrode platforms and the gel is accommodated into the chamber before such platforms are placed.

TABLE 1

Excess of reagents (ER %) used in Geneline II and MiniTAFE

| N (No. of samples loaded) | TAFE GL-II Bc = 3500 ER (%) | MiniTAFE Bc = 325 ER (%) |
|---|---|---|
| 1 | 97.5 | 87.5 |
| 2 | 95.0 | 75.0 |
| 3 | 92.5 | 62.5 |
| 4 | 90.0 | 50.0 |
| 5 | 87.5 | 37.5 |
| 6 | 85.5 | 25.0 |
| 7 | 82.5 | 12.5 |
| 8 | 80.0 | 0.0 |
| 9 | 77.5 | — |
| 10 | 75.0 | — |
| 11 | 72.5 | — |
| 12 | 70.0 | — |
| 13 | 67.5 | — |
| 14 | 65.0 | — |
| 27 | 32.5 | — |
| 40 | 0.0 | — |

—: Means that the gel does not have those wells.
ER: Percentage of reagents used in excess.
GL-II: Geneline II.
Bc: Total volume of buffer solution filling the chamber, in ml.

To implement this solution it is necessary to place the electrodes and the gel in relation to the platforms in the proper position. However, this double positioning of the electrodes in the platforms and the platforms with respect to the gel can vary the relative disposition between the gel and the electrodes. Therefore, this aspect should be improved in the design of the chambers.

As it was mentioned, in the existing chambers there are zones crossed by lines of force of the electric field that do not act directly upon the molecules loaded into the gel (non useful electrophoresis zone, NEZ). These regions do not play an essential role in the separation of the DNA molecules.

The miniequipments previously reported are not optimum, because they do not have any system to attenuate turbulences of the buffer solution flowing through the chamber neither to prepare gel without irregularities nor to form thin sample plugs of similar sizes and shapes.

Up to now, the attention has been focused on maintaining constant the voltage across the electrodes of the chambers during the electrophoresis. It is particularly notorious in the CHEF chambers, in which is necessary to set a given voltage value in each electrode of the hexagonal array. However, the quality of the band patterns and the experimental reproducibility are affected by variations in the voltage and other factors The reproducibility of the band patterns is also affected by the factors that provoke non-homogeneity of the current flowing through the buffer filling the chambers and the factors that could distort the lines of force of the electric field.

These other factors have not been completely considered in PFGE systems For this reason, the current systems can give as results distorted band patterns. These problems are relevant in the miniequipments for electrophoresis. They are:

The chambers do not have simple devices to attenuate the turbulences of the buffer flowing through the chamber and the external heat exchange.

The accessories to cast the gels do not avoid the formation of irregularities and defects in the electrophoresis gel.

The accessories to immobilize the DNA molecules in the agarose plugs do not warrant the formation of sample plugs with dimensions similar to those of the wells of the agarose gel. There are not devices to achieve a good alignment of the sample plugs in the migration origin either.

There are not devices to warrant maintaining the electrodes stretched.

The mentioned aspects affect the obtainment of straight and reproducible band patterns in the different lanes of the gel. These aspects also affect the band pattern reproducibility during different electrophoresis runs in the same or in several equipments.

On the other hand, the chambers for pulsed field gel electrophoresis are filled with a buffer solution that is circulated between the chamber and an external heat exchanger From the potential applied across the electrodes is generated the electric field or driving force of the molecules and the buffer solution is the medium through which the electric field is established. The physicochemical processes occurring in the buffer during the electrophoresis, as the electrolysis, the buffer heating by Joule-effect and the variations of the concentration of the ions of the buffer provoke non-homogeneities in the conducting properties of the buffer solution. The temperature, concentration and others variables affect the viscosity of the buffer, and thus the electric field generated through the buffer as well as the movement of the DNA molecules Thus, DNA migration is affected in different fashions throughout the chamber, when any of these variables are randomly changed The electrolysis also affects the buffer conductivity. The buffer in the chamber is constantly exchanged with thermostated buffer at constant temperature. It is accomplished by using a peristaltic pump. Therefore, it is intended to maintain homogeneous and constant the properties of the buffer solution. The buffer flow velocity should warrant the total exchange of the chamber's buffer in a few minutes. However, at a given buffer injection velocity, turbulences in the chambers are generated. Then, local non-homogeneity of the applied electric field is generated, which affects the movement of the DNA molecules The resulting band patterns depend on the variations of the conductivity in the buffer solution of the chamber and the presence of turbulences in that buffer. The turbulences are increased if the buffer is circulated at high flow velocities. The turbulence, vortices or waves locally change the height of the buffer, modifying randomly and regionally the electric resistance values of the buffer in the chamber. The variations in the electric current flowing through the different regions of the chamber modify the DNA migration and generate distorted DNA band patterns.

The equipment CHEF MAPPER from Bio-Rad considers this problem (CHEF Mapper XA Pulsed Field Electrophoresis System. Instruction Manual and Application Guide p 4. Bio-Rad). The Bio-Rad CHEF has two small chambers below the main chamber floor at the front and rear of the main chamber. They are used for buffer circulation and priming the pump. Buffer enters the main chamber through six holes in the floor near the top. A flow baffle just in front of these holes prevents gel movement. However, this system is not efficient to attenuate buffer turbulence, mainly when high flow velocity is used Neither the TAFE nor the miniequipments have any system for attenuating the turbulences of the buffer flowing throughout the chamber, which is a disadvantage. It is easy to sense that the turbulences are more harmful in the miniequipments that use less amount of buffer. For example, the turbulences in the CHEF Mapper chamber, filled with 2.2 L, are attenuated easier than in the miniCHEF and miniTAFE that use ten times less buffer As it was mentioned, the PFGE large chambers attenuate in certain extent the height of buffer oscillations. However, the miniequipments for PFGE are relatively recent. maybe for this reason the development of a system for attenuating the turbulences of the buffer flowing through these chambers has not been a focus of attention.

The gels used in the CHEF and TAFE equipments of large dimensions as well as in the mini-equipments matches with the mold where they are cast, a comb is inserted and the molten agarose is poured. While the agarose is solidifying, the mold is not covered. Then, because of the surface tension of the molten agarose, it wets the walls of the mold forming a meniscus The meniscus is formed between the wells of the gel or in the walls of the gel mold. The mold to prepare the TAFE gel has a lid, but it has not accessories to avoid the meniscus formation among the teeth of the comb. The accessories to pour the gels of the miniCHEF and miniTAFE do not have cover, and then the meniscuses are formed in the sites above-mentioned.

The gel is the medium through which occurs the migration of DNA molecules during the electrophoresis. The presence of meniscuses at the edges of the gel or between the wells of the gel modifies the electric resistance in the gel and consequently the electric current The regional changes of the electric current flowing through the gel affect the DNA migration in such regions. These changes are essential if meniscuses are formed The gel wells are the origin of migration of the molecules; consequently, if the irregularities in these zones provoke changes in the velocity of migration of the molecules, the migration boundaries will be distorted. Then, these distortions will be maintained during the electrophoresis process, finally giving distorted patterns in the gel lanes Any gel irregularity in any other region will also affect the molecule migration through such region From the point of view of the band pattern reproducibility, the accessories to prepare the gel and the method to use it are important. The designs of efficient systems for pulsed field gel electrophoresis has been focused in afford chambers with different electrode configurations and an electronic circuitry suitable to switch the electric field and impose the voltages. The properties of the accessories to prepare the gels have not been exhaustively considered As it was mentioned, the pulsed field gel electrophoresis includes the methodology for the preparation of intact DNA molecules immobilized in gel plugs. To do it, it is necessary to have molds to form the sample plugs.

The existing molds are the following:

A mold to form similar and single plugs (Cantor C. R. and Schwartz D. C., U.S. Pat. No. 4,473,452);

A mold to forms long and flat ribbons that are cut to provide single plugs;

A mold to form long agarose rods that are cut to provide single plugs (Birren B. and Lai E. Pulsed Field Gel Electrophoresis: A Practical Guide, Academic Press, New York, 1993, 29–30).

Usually, the above molds generate sample plugs of dimensions larger than the wells of the gel. For this reason, it is recommended to cut the plugs with the aid of a blade or other instrument (CHEF Mapper XA Pulsed Field Electrophoresis System. Instruction Manual and Application Guide p 40, Section 7. Catalog Numbers 170–3670 to 170–3673. Bio-Rad).

In the current chambers (CHEF, TAFE, miniCHEF and miniTAFE), the inequalities of the sample plugs provoked by cutting them after their preparation, affect the quality of the electrophoresis patterns. It is known that the sample plug thickness has influence upon the DNA resolution and the electrophoresis time. However, the effect of the shape and dimension inequalities of the sample plugs upon the electrophoresis patterns has not been thoroughly studied. The effects provoked by a bad alignment of the sample plugs lengthwise the origin of migration have not been studied yet. The researchers have used the sample plugs makers mentioned in the above paragraph. However, these molds do not include devices to cut the sample plugs with identical shape and dimensions and matching with the gel wells.

If it is considered that the band patterns obtained in each gel lane at the end of the electrophoresis depend on the fact that molecules of similar sizes are moving together from the wells toward the bottom of the gel, the importance of the accessories to prepare the sample plugs and align them in the gel wells will be understood. That is, the migration boundary should move forming a thin and straight band. When the migration boundary is deformed in the origin of migration, it will be maintained deformed during the electrophoresis, because in the chamber does not exist any device or force to correct the movement. The flaws preparing the sample plugs and troubles in their alignment in the gel wells are exactly reproduced in the bands separated in the patterns, and might provoke tilted and undulated bands.

In the U.S. Pat. No. 5,457,050 of 1995 of G H Mazurek, was disclosed a mold and a processing chamber to perform the cell immobilization and treat the cells inside the mold. Depending on the material used to construct such mold, it could be disposable or reusable. Besides that sample plug preparation could be longer using this processing chamber, said mold does not have associated a device to cut the sample plugs and, thus, plugs of similar sizes are not warranted to be obtained.

On other hand, the equipments TAFE Geneline I and Geneline II fix its four platinum electrodes between two parallel acrylic sheets (Beckman, The Geneline System Instruction Manual, ed. Spinco Division of Beckman Instruments, 1988). One of the end of each electrode goes toward the lid of the chamber, outside of the useful electrophoresis zone. It is done with the aim of connecting the platinum wire to a plug in the lid of the chamber. In this way, it is warranted the electrical continuity between the circuitry and buffer solution as well as the polarization of the electrodes. The platinum wire in the lid is insulated with a plastic capillary with high dielectric constant. As it is known, the platinum electrodes become thinner during pulsed field gel electrophoresis and during their use, the electrodes slacken and become bent and undulated for several zones Them, the system used in the TAFE to set the electrodes has the disadvantage that to pull tight the electrode the experimenter must dismount the electrode from the lid and this is very difficult.

When the electrodes become bent, undulated or slacken, the equipotential lines in the gel and the force lines of the electric field become also distorted provoking that bands do not migrate in a sharp and straight boundary.

By the other side, the way to fix the electrodes in the TAFE equipments wastes a portion of platinum wire. For example, the Geneline I uses approximately one meter of platinum wire, while the active electrodes require only thirty centimeters. The Geneline II has a similar design.

In the CHEF Mapper, the electrodes (J-shape) are fixed on supports made of material with high dielectric constant, in such a way that one of its ends passes through the support (CHEF Mapper XA Pulsed Field Electrophoresis System. Instruction Manual and Application Guide p 4 and 65, Section 7. Catalog Numbers 170-3670 to 170-3673. Bio-Rad). The supports are inserted into the floor of the chamber. In this way, the platinum wire passes through the floor of the chamber and is connected to the circuitry to clamp the voltage across the electrodes. To seal the floor of the chamber a silicone sealant and rubber O-rings pressed down with a nut are used. The fixing of electrodes in the CHEF Bio-Rad saves platinum wire because the electrodes are not so large and they do not have to pass out of the buffer. However, it is not warranted that these electrodes are maintained stretched and consequently slight deformations of the lines of force of the electric field can occur.

The disclosed MiniTAFE and MiniCHEF equipments (Riverón A. M. et al., Anal. Lett, 1995, vol. 28, 1973–1991; European Patent Application EP 0 745 844, Bull. 1996/49) have extended the electrode platinum wire above the buffer solution level in the chamber as the TAFE equipment does. In this way, it is warranted the necessary communication between the electrodes and the electronic circuitry to polarize them. The regions of the platinum wire that do not act as electrode are insulated with tubing made of material with high dielectric constant to avoid the contact of such platinum wire with the buffer The TAFE chamber uses electrodes that are at least as long as the width of the gel and are suspended between the sidewalls of the chambers. During the use, the electrodes slacken and undulated, so the band patterns can be distorted. Besides, it represents an additional expense of platinum wire and them the chambers are more expensive.

MiniTAFE equipments separate the S. cerevisiae chromosomes at high electric fields (22 V/cm), giving a suitable resolution between the bands of the electrophoresis patterns in the minigels (Riverón et al., Analytical Letters, vol. 28, p 1973–1991, 1995). Besides it, using the miniTAFE the S. cerevisiae chromosomes can be resolved in 5 hours, at 8 Volt/cm and 20° C. Small separation between opposite electrodes permits the construction of small chambers and the use of small buffer volume to cover the electrodes (350 ml) When across the miniTAFE electrodes a given voltage is applied, that is, a certain value of electric field strength 'E' is applied, then the heat dissipation is less than those obtained in TAFE equipments if the same 'E' would be applied. The samples plugs loaded into the minigels of the mini-equipments need small amount of biological material and the plug thickness ranges from 0.1 to 0.05 cm. They reduce the electrophoresis time and contribute to give sharp bands in the patterns (López-Cánovas et al., J Chromatography A, 806, p 187–197, 1998). In the minigels can be loaded as many sample plugs as permitted by the minigel width. For example, for a gel of 4.0×4.0×0.5 cm (width, height and depth) can be loaded up to 10 sample plugs of 2.5 mm in width and spaced apart 1 mm Despite of the mentioned advantages, the refereed equipments have inadequacies that limit their application in the analysis of numerous samples. In particular, when the number of samples to be analyzed changes considerably among the experiments. Several of these inadequacies are related to the shape and arrangements of the chamber dimensions as well as the existence of a single UEZ.

There are methods to select the run conditions in the PFGE equipments. For example, the CHEF Mapper from Bio-Rad has both auto-algorithm and interactive algorithm options (CHEF Mapper XA Pulsed Field Electrophoresis System. Instruction Manual and Application Guide. 31-40 Catalog Numbers 170-3670 to 170-3673. Bio-Rad). Both options permit to calculate the pulse time, the duration of the ramps of pulse time, reorientation angle, electric field and the optimum electrophoresis time to separate the DNA molecules of a given sample In contrast to the auto-algorithm, that assumes constant values for the variables, the interactive algorithm permits to change the time, temperature and concentration of the buffer and the type and concentration of agarose Both algorithms make the calculations based on empiric and theoretical data, collected during five years of experiences (Bio-Rad Catalogue. Life Science Research Products 1998/99. Bio-Rad Laboratories, 185). However, the manufacturers recommend entering to the auto-algorithm DNA sizes lower and larger than the limits of the range to be optimized. They also recommend to be considered that both algorithms can give erroneous results such as DNA mobility inversion in the mid-range of the gel, when extremely wide size ranges are entered in both algorithms.

There are other empirical expressions giving the pulse time that would separate a group of molecules which sizes are between a given size and other superior one called RSL (Resolution Size Limit) (Smith D. R. Methods 1, 1990, 195–203). However, this relation is only valid in some experimental conditions and does not predict the resolution between any pair of molecules. There is also a function calculating the approximate conditions of the electric field and pulse time that separate a given set of molecules (Gunderson K. and Chu G. Mol. Cell. Biol., 1991, 11, 3348–3354). It should be noted, that such function only permits to estimate the approximate values of these two variables, but does not give the migration of the molecules at any experimental condition.

Despite many theoretical studies about the reorientation of the DNA molecules during PFGE have been performed (Noolandi J., Adv. Electrophoresis, 1992, 5, 1–57; Maule J., Mol. Biotech., 1998, 9, 107–126), they have not given practical results, useful in the laboratory It means that they do not generated methods that permit the easy selection of the experimental conditions that separate a given group of molecules.

The equations proposed by López-Cánovas L. et al (López-Cánovas L. et al., J. Chromatogr. A, 1998, 806, 123–139) to describe DNA migration in PFGE have not been extended to select the experimental conditions applicable in any equipment when the pulse time, electric field and temperature varies.

Up to now, the experimental conditions applicable in PFGE equipments are the result of the experience of the PFGE's user, more than the results of equations describing DNA migration in PFGE. There is not a secure method to predict the pulse and run times hat should be applied at any conditions. That method is particularly important when the minichambers of the mini-equipments are used, because in the miniequipments can be used high electric field strength. The use of such high electric field strength is not frequent in the rest of the PFGE systems.

DETAILED DESCRIPTION OF THE INVENTION

The present invention refers to chambers for pulsed field gel electrophoresis of the 'Contour Clamped Homogeneous Electric Field' (CHEF) or 'Transversal Alternating Field Electrophoresis' (TAFE) systems, the accessories and the methods for their use The chambers of this invention are used to separate large DNA molecules by pulsed field gel electrophoresis (PFGE), done in miniequipments and minigels, as well as in chambers using multiple minigels. Chambers, accessories and methods herein disclosed have applications for typing strain collections of the food industry, as well as strain collections of scientific research and clinical microbiology laboratories. They also find applications in molecular epidemiological studies and in the determination of sources of contamination in the biotechnological industry. The chambers can be used to type multi-drug-resistant bacteria, to characterize the genome of mammalian and vegetable species as well as to study human hereditary diseases. In this last application, new rapid and reproducible diagnosis methods can be developed.

The present invention provides pulsed field gel electrophoresis chambers of the CHEF and TAFE systems. They have optimal dimensions and permit to apply high electric fields.

They also permit to perform co-electrophoresis of many or few samples in multiple minigels as well as to reduce the running time duration maintaining the resolution among the molecules and the high-throughput capacity of analysis.

In the invention, it is assumed the existence of systems to energize the electrodes with the proper voltage values that should be set in CHEF and TAFE chambers. A system, as the one reported by Maule (Maule J. and Green D. K. Anal. Biochem. 1990 191, 390–395) or other similar, is suitable for the proper electrode polarization. It is also assumed that are available a power supply, an external heat exchanger, a circulator to thermostat the buffer solution in the chamber, as well as the chemical and biological reagents to carry out the electrophoresis process of the large DNA molecules.

The invention, disclosed herein, provides:

Minichambers for pulsed field gel electrophoresis (PFGE) in the CHEF and TAFE systems, having a single useful electrophoresis zone (UEZ), from which the non-useful electrophoresis zones (NEZ) have been eliminated. The minichambers circulate the buffer solution at high flow velocity but avoiding turbulences in the buffer flowing throughout the chamber. They also permit the fast separation of the molecules in band patterns that are reproduced in all lanes of gels, band patterns that are also reproduced among electrophoresis performed at different moments.

TAFE multiminichambers, having separations between the opposite electrode pairs as those of minichambers, two or several UEZ that accommodate a minigel each one, and chambers from which non-useful electrophoresis zones were eliminated. These chambers have a high-throughput capacity of sample analysis but they can analyze few samples maintaining its optimization and rapidity of analysis. It is foreseen that the reagent consumed in these chambers depends on the quantity 'N' of samples that is going to be analyzed in each experiment. It is also foreseen that the user can vary the number of UEZ that will be used in each experiment and the shortening of the electrophoresis running time.

Accessory sets to attenuate turbulence of then buffer flowing throughout the chamber, to prepare minigels of flat surfaces, with the absence of irregularities, as well as to cast sample plugs of homogeneous shapes and sizes similar to those of the gel wells into which they will be loaded.

Methods for using the pulsed field gel electrophoresis chambers, methods that include a method to calculate the electrophoresis run time at any values of electric field and temperature used in the chambers.

The chambers, accessories and methods of this invention, permit the fast separation of large DNA molecules in minigels, using agarose in a concentration range between 0.5 and 1.5%. In particular, the chambers, accessories and methods provided herein have the following distinctive characteristics:

They use of rectangular or square shaped minigels into which can be loaded up to 200 sample plugs. The number of samples depends on the minigel width, which in turn, depends on the separation between the electrodes with opposite polarity in CHEF chambers and on the width in the TAFE chambers. The volume of buffer solution also depends on the separation between electrodes with opposite polarity and the width of the chamber.

The chambers provide reproducible results because the chambers as well as the accessories warrant homogeneous electric current throughout the buffer solution and good alignment of the sample plugs in the migration origin. They also warrant stretched electrodes.

The chambers are able to separate rapidly, at least in 2.5 hours, the DNA molecules of sizes up to 2 megabase pairs.

The chambers are provided with a method to calculate the electrophoresis run time, if the electric field, temperature and pulse time applied in the electrophoresis process are provided A.—The Calculation of the Minigel Dimensions, the Area of the Chambers and the Number of Samples That Can be Loaded into the Wells.

To perform these calculations, we will name 'd' to the separation between the pairs of electrodes with opposite polarity The dimensions, recommended for the width and length (in cm) of the CHEF minigels, as well as the area of the floor of the chamber without NEZ regions and having a single UEZ with a hexagonal array of electrodes, are given by $$\text{width of the rectangular minigel} = d/(2 \cdot \cos(30°))$$
$$= d/1.732$$
$$\text{length} = d \cdot \{1 - 1/[2 \cdot \cos^2(30°)]\}$$
$$= d/3$$
$$\text{side of the square minigel} = d \cdot \{1 - 1/[2 \cdot \cos^2(30°)]\}$$
$$= d/3$$
$$\text{area of the chamber floor} = [2 + (d/\cos(30°))] \cdot [6 + d]$$
$$= [2 + (d/0.87)] \cdot [6 + d]$$

NEZ regions were eliminated from the chamber, because they do not play an essential role in the separation of DNA molecules. In addition, the chamber side walls should be separated 1 cm from the electrodes, and the system for attenuating turbulences of the buffer flowing throughout the chamber flow (explained further) should occupy 2 cm in the buffer inlet and outlet regions. These considerations explain the constant values of 2 and 6 in the formulas of the area of the chamber floor If 'd' is between 6.2 and 15 cm, then the width 'a' of rectangular-shaped minigels is comprised between 3.6 and 8 7 cm.

the length is between 2.1 and 5 cm, the area is between 7.6 and 43.5 cm$^2$, the side of square/shaped minigels is comprised between 2.1 and 5 cm, the area is between 4.4 and 25 cm$^2$, the area of the floor of the chamber is between 111.3 and 404.1 cm$^2$ The buffer level in the chamber must surpass 0.3 cm the minigel height, thus the amount of buffer volume is defined by:

buffer volume=$\{[2+(d/\cos(30°))]\cdot[6+d]\}\cdot(0.3+\text{minigel thickness})$ If the minigels thickness is between 0.35 and 0.5 cm, then the amount of buffer volume will be between 72.3 and 323.3 ml.

The maximum number of plugs that can be loaded in minigels is defined according to their width 'a' (in cm) as:

number of plugs to be loaded in the minigels= $(a-0.2)/0.25$

Where, for rectangular-shaped minigels of 3.6 and 8.7 cm, the maximum number is comprised between 13 and 34 plugs, respectively.

The length (in cm) of TAFE minigel in minichambers that have a single UEZ or several UEZ (multiminichambers) is:

$$\text{length of the minigel} = d \cdot \sin(31°)$$
$$= d \cdot 0.515$$

and the minigel width 'a' is the width of the UEZ. When the TAFE chambers have a single UEZ, the minigel width coincides with the chamber width; whereas, if the chambers have larger number of UEZ, the multiminichambers will have two or several minigels, being their widths equal to the width of each UEZ.

The area (in cm$^2$) of the walls supporting the minigel and the electrodes is given by area=$[2+1.4\cdot d]\cdot[2+0.54\cdot d]-1.02\cdot[1+0.54\cdot d]^2$ If 'd' is between 6.2 and 15 cm, the minigel length will be between 3.2 and 77 cm, whereas the area of each wall, supporting the minigel and the electrodes, will be between 37.8 and 147.8 cm$^2$.

In TAFE chambers, the less is the distance 'd' between the pairs with opposite electrodes, the less is the cross section area, and, thus, higher electric fields could be applied without significant increments of the initial electric current '$I_o$' and the power in the chamber Therefore, to construct TAFE chambers having large width 'L' (chamber width or dimension parallel to electrodes), it is convenient that the distance 'd' be small This warrants that 'E' values separating fast the chromosomes without '$I_o$' surpassing the maximum output of the conventional PFGE power supplies may be applied.

Although the chambers have small separations between opposite electrodes. optimal chambers are only those that are wide enough to support simultaneously several minigels, which can be excluded (or not) from the experiments at will as well as the corresponding buffer volume. The subdivision of a very wide minigel in several less wide minigels is attained efficiently if the chamber is subdivided in several UEZ. If all samples that the minigels admit are loaded into them, then the chambers will be functioning at full capacity, analyzing simultaneously many samples However, if few samples would be analyzed. its capability of analysis would not be put in good use and the reagents would be wasted To avoid it, only the required UEZ must be activated, and the non-used UEZ should be excluded. In that way, the volume of reagents used in each experiment will depend on the number of samples to be analyzed and, therefore, on the number of UEZ activated.

The maximum number of samples that can be simultaneously analyzed in the TAFE minigels depends on the size and number of UEZ, which in turn depends on the maximum width ('L') of the chamber. The chamber width determines the electric current withdrawn from the power supply. Thence, the limiting factors for constructing wide TAFE chambers are the electric current and power outputs of the power supplies available. Thus, the knowledge of the power supply characteristics permits to calculate 'a priori' the maximum width that TAFE chambers could have, if equations describing the electric current circulating through the chamber are available.

To obtain the equations describing the electric current circulating through the chamber, a TAFE chamber was constructed. It has a distance between the pairs with opposite electrodes in the range defined for TAFE minichambers and 316 mm width ('L'). NEZ were eliminated from this chamber, and accessories were designed to permit to vary the inner dimensions of the chamber from 7 cm to the width 'L' of the chamber, thus, allowing to have 'n' TAFE chambers of different widths. To obtain the equations, the specific conductance 'p' (mho.cm$^{-1}$) of 0.5×TBE buffer (1×TBE: 89 mM Tris, 89 mM boric acid and 2 mM EDTA, pH 8.3) is fitted to a function of the Tris molar concentration and the experimental temperature 'T' (° C.):

$$\rho = 5.190 \cdot 10^{-3} \cdot [\text{Tris}]^{0.8461} \cdot e^{0.02214 \cdot T} \qquad (II)$$

Here, the initial electric current '$I_o$' (in Amperes) flowing through the chamber was taken as depending on the electrolyte resistance, which is given by the relation between the vessel constant 'Cv' (in cm$^{-1}$) and the specific conductance 'ρ'. The vessel constant depends on the separation between electrodes with opposite polarity and on the cross section area 'A' (cm$^2$) that the chamber presents to the flow of the electric current.

The chambers do not have regular geometric shapes due to the elimination of the NEZ; therefore, the vessel constants (Cv=d/A) need to be determined for different widths and shapes. To determine them, the following procedure was developed:

The cell constant 'Cv(cond)' of a conductivity meter is determined.

The chamber is filled with a solution of any given electrolyte, which is maintained at fixed temperature.

The conductivity of said electrolyte is measured using the calibrated cell of the conductivity meter 'G(cond)'.

The conductivity of said electrolyte is measured by connecting the electrodes of the electrophoresis chamber to the measuring plugs of the conductivity meter 'G(chamber)'.

It is easy to deduce that 'Cv(chamber)' is:

$$Cv(\text{chamber}) = [G(\text{cond}) \cdot Cv(\text{cond})] / G(\text{chamber}) \qquad (III)$$

For each of the 'n' TAFE chambers having different width '$L_1$' (where 'i' is between 1 and 'n') '$Cv(chamber)_i$' is determined. Then, the function relating '$Cv$' and '$L$' can be obtained $$Cv(chamber)_1 = f(L_1) \quad (IV)$$

Hence, in chambers of '$L_1$' width, the electrical resistances '$Re_i$', given by electrolytes of '$\rho_j$' conductivity, are given by:

$$Re_i = Cv(chamber)_1/\rho_j \quad (V)$$

Since the initial studies on conductivity, it is known that if a voltage is applied using a direct current power supply, the measured electric current flowing through the electrolyte does not depend on '$Re$' alone. In fact, polarization of the electrolyte occurs, thus, reducing the values of the electric field and the circulating electric current. For this reason, to design TAFE chambers of variable width, functions describing the attenuation of the electric field due to electrolyte polarization must be available.

The electric field attenuation in the electrophoresis chambers of different widths and geometric shapes can be estimated if '$Re$' is known (equations II, IV y V) and if it is considered that the resistance (R) measured in the buffer solution filling the chamber can be modeled as two resistances in series, '$Re$' and '$Rp$'

$$R = Re + Rp, \quad (VI)$$

where '$Rp$' plays the role of an additional resistance induced by electrolyte polarization Then, according to Ohm's law $$V_{DC} = I_{DC} \cdot R \quad (VII)$$

where $V_{DC}$ is the voltage applied using the direct current power supply and $I_{DC}$ is the direct current measured: If increasing values of $V_{DC}$ are applied and $I_{DC}$ values are measured, then '$Rt$' values can be calculated and '$Rp$' estimated from the knowledge of '$Re$' values (equation V) in that chamber. In that way, the function relating '$Rp$' to '$Re$' and to '$V_{DC}$' can be obtained $$Rp = f(Re, V_{DC}) \quad (VIII)$$

By using the above equations, it is possible to predict the initial currents ('$I_0$') that would be withdrawn applying $V_{DC}$ voltages to chambers having different widths and filled with buffer solutions of different conductivities and setting the electrophoresis at various temperatures. Therefore, the maximum width that each chamber could have can be estimated for each existing power supply of known electric current, voltage and power output. The best chamber width is the one, which withdraws electric current '$I_0$' and power '$P$' that do not surpass the maximum output values of the power supply. The voltage to get that '$I_0$' or that '$P$' is the maximum voltage that can be applied in said chamber To design TAFE multiminichambers, the prediction of '$I_0$', is not enough, it is also necessary to consider the buffer exhaustion. That is, the increments of the electric current circulating through the buffer of the chamber, due to buffer exhaustion should not surpass the electric current and electric power limits of the power supply during the electrophoresis. For that reason, it is necessary to develop equations describing buffer exhaustion as the electrophoresis time elapses. The time needed to exhaust the buffer should depend, at least, on '$E$'. The equation describing the buffer exhaustion constant ('$k$', in Ohm. $t^{-1}$) can be obtained assuming that, if a voltage '$V_{DC}$' (in volts) is applied across the electrodes, the electric current '$I_{DC}t$' (in Amperes) flowing through the chamber at any electrophoresis moment is given by $$I_{DC}(t) = V_{DC}/R(t) \quad (IX)$$

where, $$R(t) = R + kt \quad (X)$$

$$k = f(E) \quad (XI)$$

and '$R$' is calculated according to the equation VI. Thus, by the use of these equations. '$I_0$' can be predicted, as well as the variations of electric current flow during the electrophoresis., This calculation allows knowing the moment of replacing the buffer solution during each experiment. These equations can be obtained empirically, adding buffer solution into the chamber, regulating the temperature, applying the voltage across the electrodes and finally monitoring the electric current ('$It$') flowing through the buffer during the time ('$t$'). Further, regression methods are used for describing the relationship among the variables.

The relationships II to XI can be used to calculate the maximum width '$L$' of the TAFE multiminichamber, which depends on the distance '$d$' between electrodes, the conductivity '$\rho$' and the buffer temperature '$T$'. The width also depends on the applied electric field, which is restricted by the maximum electric current '$Imax$' and power '$Pmax$' outputs of the power supply used to energize the multiminichamber. That is, $$L = f(Imax, d, \rho, T, Emax) \quad (XII)$$

$$L = f(Pmax, d, \rho, T, Emax) \quad (XIII)$$

The maximum width '$L$' of TAFE multiminichambers is the smaller of the two '$L$' values obtained using the functions XII and XIII.

Based on the equations XII and XIII and using power supplies that give up to 2 amperes and 300 watts of electric current and electric power outputs, respectively, the widths '$L$' of TAFE multiminichambers can reach up to 50 cm. In said chambers, the distance between pairs with opposite electrodes can reach up to 15 cm, and 0.5×TBE buffer can be used at 30° C. as maximum temperature These multiminichambers can be subdivided in UEZ If all ZUE are used in the electrophoresis, the electric fields can be increased up to 8 V/cm, whereas if several UEZ are inactivated, the electric field can be reached up to 25 V/cm. The number of UEZ can vary between 1 and 30.

The area of the minigel of TAFE chambers that have one or multiple UEZ (multiminichambers) is:

$$\text{minigel area} = d \cdot \sin(31°) \cdot L/UEZ_{total}$$

$$= d \cdot 0.515 \cdot L/UEZ_{total}$$

the volume of the buffer solution added to the chamber depends on the width of the selected chamber, and it is calculated in the following way:

$$\text{buffer volume} = [(2 + 1.4 \cdot d) \cdot (2 + 0.54 \cdot d) - 1.02 \cdot (1 + 0.54 \cdot d)^2] \cdot L \cdot UEZ_{act}/UEZ_{total}$$

where, $UEZ_{act}$: number of UEZ activated during the electrophoresis, $UEZ_{total}$: number of UEZ in the chamber.

The subdivision of TAFE chambers in UEZ improves the efficiency of said chambers It is made evident taking again the formula I and defining:

| | |
|---|---|
| Bc: | Volume of reagents in ml (of the buffer solution or the agarose) that requires the chamber. |
| Bzue: | Volume of reagents in ml required by each UEZ, being each UEZ used to separate a maximum of 'NM' samples. |
| Bnt: | Volume of reagents in ml required when a number 'Nzue' of UEZ are activated. Bnt = Nzue · Bzue. |
| Nt: | Maximum number of samples that can be loaded in all UEZ that were activated Nt = NM · Nzue. |
| (Nt − N) | Number of samples that were not loaded in the experiment. |
| (Bnt/Nt): | Volume of reagents in ml required by each sample. |
| (Nt − N) · (Bnt/Nt): | Excess of reagent volume when 'N' samples are loaded but 'Nt' samples could be loaded. |

By relating the excess of reagent volume to the reagent volume 'Bc' needed by the chamber, and calling the result 'ER', 'ER' is:

$$ER(\%) = 100.0 \cdot Bnt \cdot (Nt-N)/(Nt \cdot Bc) \quad (XIV)$$

By applying the relation XIV to a chamber that has four UEZ, each UEZ requiring 325 ml of buffer solution and admitting a minigel supporting 13 samples, the values shown in Table 2 will be obtained for 'ER'. In the example, 'ER' ranges from a maximum value of 23 1% if 'N' is 1, 14, 27 or 40 samples, to a minimum of 0% if 'N' is 13, 26, 39 or 52 samples (Table 2). Notice that, if a single UEZ is used, the remaining three ones are inactivated and occluded, so Bnt=325 ml and Nt=13. Similarly, if the first and second miniplatforms are used only, Bnt=650 ml and Nt=26, and so on. Chambers having a single UEZ are the Geneline II, Nt=40, Bc=Bnt=3500 ml and the MiniTAFE Nt=8, Bc=Bnt=350 ml. Thus, Bc=Bnt and ER=(Nt−N)/Nt (Table 1). Therefore, the chambers must be subdivided in several UEZ, by subdividing or not the electrode platform, but maintaining the capacity to perform co-electrophoresis to the desired number of samples, and being energized with a single power supply. Additionally, they do not waste excess of reagents. In these chambers, the volume of reagents ('Bnt' in ml) used during each electrophoresis depends on the maximum number of samples to be analyzed ('Nt') in each experiment All UEZ of a TAFE chamber must be activated simultaneously using a single power supply and a single system to alternate the electric fields.

TABLE 2

Excess of reagent volume ('ER') in a chamber of four UEZ that performs transversal alternating field electrophoresis (MultiMiniTAFE) in four minigels
Bc = 1300 ml

| ZUE1 Nt = 13 Bnt = 325 N = 1 . . . 13 | | ZUE2 Nt = 26, Bnt = 650 N = 14 . . . 26 | | ZUE3 Nt = 39, Bnt = 975 N = 27 . . . 39 | | ZUE4 Nt = 52, Bnt = 1300 N = 40 52 | |
|---|---|---|---|---|---|---|---|
| N | ER (%) | N | ER (%) | N | ER (%) | N | ER (%) |
| 1 | 23.1 | 14 | 23.1 | 27 | 23.1 | 40 | 23.1 |
| 2 | 21.2 | 15 | 21.2 | 28 | 21.2 | 41 | 21.2 |
| 3 | 19.2 | 16 | 19.2 | 29 | 19.2 | 42 | 19.2 |
| 4 | 17.3 | 17 | 17.3 | 30 | 17.3 | 43 | 17.3 |
| 5 | 15.4 | 18 | 15.4 | 31 | 15.4 | 44 | 15.4 |
| 6 | 13.5 | 19 | 13.5 | 32 | 13.5 | 45 | 13.5 |
| 7 | 11.5 | 20 | 11.5 | 33 | 11.5 | 46 | 11.5 |
| 8 | 9.6 | 21 | 9.6 | 34 | 9.6 | 47 | 9.6 |
| 9 | 7.7 | 22 | 7.7 | 35 | 7.7 | 48 | 7.7 |
| 10 | 5.8 | 23 | 5.8 | 36 | 5.8 | 49 | 5.8 |
| 11 | 3.8 | 24 | 3.8 | 37 | 3.8 | 50 | 3.8 |
| 12 | 1.9 | 25 | 1.9 | 38 | 1.9 | 51 | 1.9 |
| 13 | 0.0 | 26 | 0.0 | 39 | 0.0 | 52 | 0.0 |

Considering the electric field provides the driving force in the electrophoresis, force that is much higher than the gravity, and considering that molecules do not sediment under the gravity due to their small mass; thus the molecules will always migrate toward the direction of the resultant between the field force lines of both electric fields. Therefore, the TAFE electrode array can be arranged in inverted configuration. That is, the cathodes can be placed at the bottom of the chamber and the anodes at the top, thus, loading the sample plugs in the bottom of the minigel, and provoking the molecules to migrate along the direction opposite to the gravity. This electrode arrangement will be named 'inverted TAFE configuration'. The configuration facilitates the placement of the gels in the chamber and avoids the 'double positioning' errors of the electrodes and the minigel As results given by this invention, TAFE electrophoresis chambers are provided in miniTAFE version, chambers that are wide and have multiple UEZ regions. Each UEZ can be activated at will and are all energized with a single power supply. NEZ regions are eliminated from the chambers, because they do not play an essential role in the separation of the DNA molecules. Thus, in said chambers, multiple minigels can be placed, minigels that can simultaneously separate the DNA molecules contained in few or many sample plugs, for example, in 10, 20, 30, 40 or more.

To perform the separation of these molecules, said chambers use the amount of reagents needed to analyze the 'N' sample plugs, which contain the molecules that will be separated in 't' time.

The separation between electrodes with opposite polarity is that described for TAFE minichambers, and for this reason, the chambers separate the molecules fast.

The chambers are as wide as the equations II–XIII predicted, and according to the maximum outputs of the power supplies for pulsed field electrophoresis (see the example in Table 3). For this reason, the chambers are able to separate the molecules contained in at least 52 samples of 2.5 mm width.

The chambers have several useful electrophoresis zones (UEZ) that can be used in the experiments or can be occluded and inactivated, the chamber requires a single power supply and a single system for alternating the electric fields. For this reason they use efficiently the equipments.

The subdivision of the chamber in several UEZ simulates chambers with variable width, and makes 'Nt' and 'Bnt' to vary according to the number of UEZ used in the chamber (see in Table 2 the example of a chamber with 4 ZUE). The volume of buffer solution is replaced as the equations II, III, IV and V predict. For this reason, they can analyze few or many samples using efficiently the reagents.

The chambers can be constructed in conventional TAFE configuration or in inverted TAFE configuration. They can be made with acrylic, teflon or any other material with high dielectric constant.

The non-useful electrophoresis zones (NEZ) are occluded with pieces of the proper shapes, which are made of materials with high dielectric constant. Otherwise, they could be eliminated from the chambers by means of any construction procedure.

Several chambers that have the mentioned characteristics can be constructed We named them type I and type II chambers.

The type I chambers. Type I chambers are the simplest one and, as all these chambers, they have a small separation between the electrodes with opposite polarity, they are not deep, nor tall, but they are wide. The electrodes are as long as the width of the chamber The chambers have an electrode miniplatform, which can be fixed to the chamber or can be removable. Type I TAFE chambers can have the cathodes at the top (conventional TAFE configuration) or at the bottom (inverted TAFE configuration). In the later case, sample plugs are loaded in the wells, which are in the minigel bottom, thus the molecules migrate along the direction opposite to the gravity.

The NEZ can be eliminated from the chamber by constructing the frontal walls with the proper disposition (frontal walls are parallel to the electrodes), in particular, if the electrodes are arranged in inverted TAFE configuration. To do it, said walls should form a small angle with the plane containing the anode and cathode located at the same side of the minigel. Thus, as said plane does, the walls form an angle with the floor of the chamber. NEZ are eliminated from chambers having conventional TAFE configuration by placing in it the pieces of the proper shapes and made of materials with high dielectric constant.

These chambers have several UEZ and support several minigels, which are placed widthwise, in tandem. To achieve it, frames as width as the chamber can be designed. Said frame is subdivided in less widened frames and all minigels are simultaneously cast in them. Further, the large frame is slid into the chamber and acts as support of all minigels that will be used, thus, allowing their handling. Minigels can be simultaneously cast in those frames, further removed from them, and finally placed directly into the chamber. To do it, at the center of the chamber must be pieces that are laterally grooved, through which said minigels slide. The separation between those pieces will be equal to the minigel width, that is, the width of one UEZ. For casting minigels, the frame must be placed between two flat acrylic sheets, which are prepared to place the comb Further, these pieces are clamped. The frame can have lateral notches to fix the comb in a single position.

In turn, each minigel supports a maximum number of samples that depends on its width In this way, chambers having several UEZ that support one minigel each will be available. Said chambers will be able to separate few or many samples, using a single power supply and common electrodes. The volume of buffer solution will depend on the number of UEZ used. Thus, all samples that are analyzed in these UEZ are separated in a common buffer solution, at the same temperature and voltage applied.

According to the above principles, are achieved variability of the number of minigels that can be placed in the chambers, of the buffer volume ('Bnt') used in each experiment and of the maximum number of samples ('Nt') that can be simultaneously analyzed in a co-electrophoresis.

The type II chambers. A variant of the chambers, which is proposed in this invention, avoids the use of very long electrodes. As the type I chamber, the type II has small distance between opposite electrodes, thus these chambers have little depth and height. However, each UEZ has its own miniplatform of electrodes, and these miniplatforms are arranged in tandem and are removable from the chambers. Each miniplatform uses a minigel into which are loaded as many samples as the gel width permits, width, that in turn, depends on the electrode length.

The electrodes of one or several miniplatforms can be energized using a single power supply. To do it, the electrode arrays of the miniplatforms are connected in parallel, that is, the anodes are plugged consecutively, as well as the cathodes. Differing from the type I chambers, the UEZ (or miniplatforms of electrodes) that will not be activated in an experiment can be fully occluded using pieces of shape similar to the miniplatform Those pieces are made of materials with high dielectric constant. The connection in parallel among the miniplatforms of a chamber warrants the continuity among the electrodes of these miniplatforms, and permits to perform co-electrophoresis of all samples loaded in the minigels using a single power supply and common electrodes. Thus, all sample plugs are separated in a common buffer solution, at the same experimental temperature. and applied voltage. According to these principles, among experiments, vary the number of UEZ activated in the chamber, the number of minigels used and the volume of reagents ('Bnt'). The maximum number of samples ('Nt') that can be simultaneously analyzed in a co-electrophoresis also varies among the experiments.

In type II chambers, the multiple miniplatforms of electrodes could have their cathodes at the top (conventional TAFE configuration) or at the bottom (inverted TAFE configuration) In type II chambers having electrodes arranged in inverted TAFE configuration, the buffer solution regions that are crossed by field force lines that do not act on the minigel can be eliminated with the chamber own walls. To achieve this, the frontal walls of the chamber, or walls that are parallel to the electrodes, should form a small angle with the plane containing the cathode and anode placed at the same side of the gel (or form a small angle with said plane). Thus, as it happened with said plane, these walls from an angle with the floor of the chamber.

In the construction of type II chambers, the miniplatforms can be connected or activates by any procedure. For example, to place in the lid the wires that connect neighboring miniplatforms, or to place in the lid the plugs alone, thus permitting the wires to be external to the chamber, or to place the connections in the chamber walls or directly among the miniplatforms. On the other hand, the miniplatforms can be of any shape that fits into the chamber, provided they contain the electrode array in TAFE configuration; whereas the electrodes can be arranged permanently in the chamber or they can be removable. The regions of the chamber, in which miniplatforms are not going to be activated, can be eliminated from the experiment using any procedure; placing solid or empty blocks., blocks that are fixed to the walls or filled with any liquid As it is done in the use of type I chambers, the minigels can be cast in frames.

B. The Obtainment of Reproducible Band Patterns in the Chambers Provided In This Invention.

The chambers provided in this invention are characterized by:

They have a system to attenuate turbulences of the buffer flowing throughout the chamber, system that additionally maintains constant the temperature and the homogeneity of the composition of buffer during the electrophoresis.

They have a system to insert into the electrophoresis chamber and remove from it the electrodes, system that maintains the electrodes stretched. This system uses rubber elastic plugs that are bored and inserted into holes that were drilled in the floor or the lateral walls of the chambers. The electrodes pass through the plug bore.

They have a system permitting the experimenter to pull tight the electrodes of the MiniTAFE and multiminiTAFE chambers.

In this invention are also provided a group of accessories that are relevant to obtain reproducible band patterns. They are:

An accessory set that permits to cast minigels that have flat surfaces. The system warrants the required minigel dimensions.

An accessory set that permits to align the sample plugs in the migration origin.

An accessory set that permits to prepare sample plugs of homogeneous sizes

B.1.—Systems for Attenuating Turbulences of the Buffer Flow and Homogenizing Buffer Conductivity and Temperature in the Chambers In the neighborhood of the electrodes, the buffer solution changes its conduction properties due to the electrolysis. This effect is particularly relevant in CHEF chambers that have a hexagonal array of multiple electrodes placed around the minigel For this reason, the values of buffer conductivity 'σ' in those regions of the chamber can differ from values in other regions of the chamber. This situation is critical in CHEF minichambers. The circulation of the electrophoresis buffer throughout the chamber at high flow velocity is equivalent to stir the buffer solution. Thus, said high flow velocity represents the way to warrant the homogeneity of buffer conductivity throughout the electrophoresis chamber For instance, the exchanging of the chamber volume in 3 minutes is enough for this purpose.

When the electrolyte circulates at high flow velocity, turbulences appear in the fluid of the chamber Another possible origin of turbulences of the flow is that several peristaltic pumps inject continuously small volume of buffer, as fluid pulses.

The system developed in this invention to circulate the buffer at high flow velocity, is based on the following principle. The cross section area of the buffer through which the electric current flows must be constant in the whole chamber.

The constancy of the sectional area avoids the electric current flowing throughout the chamber to be randomly modified by local changes in the buffer electrical resistance due to the presence of waves, vortices or turbulences during fluid circulation. The principle is based on the fact that the resistance (R) of any electrolyte filling the electrophoresis chamber is determined by:

The electrolyte conductivity (σ),

The separation between the electrodes with opposite polarity (d),

The cross section area that is transversal to the flow of the electric current (A)

These variables are related according to the formula XV.

$$R = (1/\sigma) \cdot (d/A) \qquad (XV)$$

Thus, if 'A' varies in different zones of the chamber, 'R' differs too and also the electric current 'I'.

The system for avoiding turbulences of the buffer flowing through CHEF chambers is composed by:

two types of rectangular sheets, one of A type and the other of B type, being both made of any material with high dielectric constant, sheets, which are as wide as the internal width of the chamber, being those of A type of 2 cm height at least, and those of B type of 0.5 cm height, A type sheets, which are separated from the floor of the chamber a distance of 0 02 to 0.05 cm, and always protrude from the buffer solution filling the chamber, thus determining that during buffer circulation throughout the chamber, the buffer can only flow through the gap formed between the A type sheets and the floor of the chamber.

B type sheets, which are glued to the floor of the chamber and fully submerged in the buffer solution, thus determining that during buffer circulation throughout the chamber, the buffer can only run flowing over the B type sheets. Both types of sheets being assembled in the chamber regions near the inlet and outlet tubing system. They are assembled from the inlet or outlet tubing system toward the electrode array in the electrophoresis chamber with the following order. A type sheet followed by B type sheet, and repeating 'n' times the sheet pair, being 'n' an integer between 1 and 4, and assembling the last sheet apart from the electrodes approximately 1 cm, last sheet that has to be of A type.

In this way, the fluid, pumped from the heat exchanger, crashes against the A type sheet when it enters into the chamber, and then it flows under this sheet. Afterwards, the fluid crashes against the B type sheet and flows over this sheet. These events are repeated at each pair of sheets of the system for attenuating turbulence of buffer flow, until said buffer flows into the compartment where the electrodes and the minigel are placed and thus runs across it. Further, the buffer solution suffers the same crashing process at the outlet region of the chamber from which the buffer is withdrawn to the heat exchanger. In this way, the turbulences that could exist in the fluid are attenuated.

The system for attenuating turbulence of the buffer flowing throughout the buffer TAFE chamber is formed by:

two identical sheets which are of the size of the chamber walls that are parallel to the electrodes.

said sheets that are made of a material with high dielectric constant, having them a horizontal slot in its third inferior part.

slot which is as long as the electrodes and has 0.3 cm in height.

The sheets of this system are placed near to the inlet of the buffer solution and near to the outlet of said solution. In that way, the sheets divide the chamber in three compartments. the central one that contains the electrodes and the minigel, and the two others, into which the tubing for circulation enters or leaves the chamber. During circulation, the buffer solution enters directly into one of these compartments, and then flows through the slot into the electrophoresis compartment. From the electrophoresis compartment, the buffer flows through the slot of the other sheet into the outlet compartment. From this last compartment the buffer returns to the heat exchanger. In this way, the turbulences that could exist in the fluid surface are attenuated.

B.2.—Set of Accessories to Warrant Homogeneity of the Electric Current Flowing Through the Minigel.

Following the above reasoning, it is realized that if the gel, or supporting medium, where the electrophoresis is done, has irregularities, it will present to the electric current flow a cross section area (A) that is different among its distinct regions. Therefore, 'Rm' (resistance to the electrical current flow through the gel) has to be maintained constant in all regions of the gel.

The accessory set to cast minigels that have flat surfaces is a disassemblable device composed by:

A flat base plate.

Two frames, one of them with a cavity that is rectangular in shape and the other with a cavity that is square in shape of 0.35 to 0.5 cm in thickness, having they two notches to fit into them a comb with long teeth while casting the minigels with its wells. Being the frame thickness and the inner dimensions of the cavities, the ones which determine the minigel dimensions that is going to be cast and used as supporting medium in the electrophoresis in CHEF or TAFE chambers.

two covers, the cover 1 or cover that fits in the frontal part of the comb, and the cover 2 or cover that fits in the rear of the comb.

A second comb that is similar to the above mentioned, but has shorter teeth and permits to push the loaded samples into the minigel wells.

The combs with long teeth, that form the wells in the minigels, are fully plain and continuous with the teeth in their frontal surfaces, whereas in the back surfaces and over the teeth they gain thickness, forming a step. The combs provided herein, have similar teeth with thickness comprised between 0.03 and 0.1 cm, teeth width between 0.15 cm and the minigel width minus 0.3 cm, and lengths of the teeth equal to the minigel thickness minus 0.15 cm. Thus, when the comb, the frame and the flat base plate are assembled, the teeth are 0.1 cm apart from the base plate and the rear step is 0.1 cm higher than the frame. The combs with short teeth are similar to the combs with long teeth, excepting that their teeth are 0.2 cm shorter.

The cover 2, or the cover that fits in the rear of the comb, has two flat sides In one of its end, it has a protruding edge that will fit in the frame during the assembly of the set The cover 1, or the cover that fits in the frontal part of the comb, has two flat sides, but one of them has a bevel edge in wedge formation.

The set is used in the following way:

on the flat base plate is placed one of the two frames, specifically the one that has the size of the minigel that will be prepared, the legs of one of the combs with long teeth are fitted into the notches that has the frame in its outer sides, giving as result that the teeth were separated 0.1 cm from the surface of the flat base plate, the cover 1, that fits in the frontal part of the comb, is placed on the frame in front of the comb, with the flat surface turned to face the frame and with the bevel edge against the comb, said accessory set is clamped, aided by any procedure, the covers are pressed against the frame, until the interstices formed between them are sealed, and then, pouring at the proper temperature the molten gel, temperature that is between 65 and 70° C. when molten agarose is used, the cover 2, or cover that fits into the rear of the comb, is placed on the frame, in the back of the comb, introducing the protruding edge of the cover into the rear step of the comb with long teeth, and then, the agarose is set to rest until solidification.

the comb with long teeth is removed, and on the wedge-shaped edge of the cover 1, or cover that fits in the frontal part of the comb, are placed the plugs containing the immobilized DNA molecules, plugs that are pushed with the aid of any applicator to let them slide into the wells.

once the sample plugs were loaded into the minigel wells, said plugs are pushed down the bottom of the wells aided by the comb with short teeth, being it accomplished by fitting the legs of the comb into the notches of the frame Thus, it is warranted to cast minigels that have flat surfaces and no meniscus, minigel in which all sample plugs were loaded at the same height and are evenly separated from the frontal or the rear edge of the minigel. Such results are obtained without the disruption of said plugs.

The accessory set to cast minigels with flat surfaces as well as the system to attenuate turbulences of buffer flow avoid that the cross section area of the minigel varies out of control because of the formation of meniscuses in the sides of the gel or among the wells of the minigel.

B.3.—Set of Accessories to Form Sample Plugs of Homogeneous Sizes.

Even the values of 'R' are warranted to be constant in the buffer filling the chamber as well as in the minigel; if the agarose plugs, containing the immobilized DNA molecules, do not have similar dimensions and are not intact, nor aligned, nor evenly separated from the rear or the frontal minigel edges, the resulting band patterns will be distorted.

The accessories to prepare DNA samples immobilized in agarose plugs of homogeneous dimensions and sizes similar to the gel wells, into which they will be loaded, are composed by:

sample plug makers, consisting each of a flat impermeable block thicker than 0 5 cm, block that is made of any material and has multiple parallel grooves, being each groove of 0.2 cm width and matching its depth with the thickness of the teeth of a given comb, depth that can be between 0.03 and 0.1 cm, existing blocks for all possible thickness of the teeth of all combs that can be used to form the wells in the gel, a flat, rigid and impermeable sheet of at least 0.1 cm thickness, which plays the role of the cover of the block, sample plug cutters, each being a bar that is as long as or longer than the grooves of the block of the sample plugs maker, said cutters having legs in the ends which confer them an inverted-U shape, said cutters having several protuberances with cutting edges In its inferior part, said protuberances protruding 0.1 cm from the bar, said cutting edges being transversal to the longest dimension of the bar and 0.2 cm in length, said cutting edges being evenly spaced a distance that is from about 0.15 to the gel width minus 0 3 cm, they has a method of using.

The use of these accessories has the following steps:

an agarose cell suspension is prepared and maintained at 45° C., whereas the sample plug maker and its cover are warmed at 45° C., said cell suspension is poured into the grooves of the block of the sample plug maker.

the block is covered with its cover and is maintained at room temperature or lower temperature, until the gel is solidified once the gel is solidified, the sample plug cutter is placed aligned lengthwise on the first groove, with the protruding cutting edges turned to face the groove and placed transversally to the largest dimension of the groove, the sample plug cutter is pressed down, the sample plug cutter is removed, the block is tilted and the plugs are pushed into a vessel that contains the proper solution to treat them, the process is repeated for all strips of agarose solidified in all grooves of the block.

By this procedure, it is warranted that the formed sample plugs were similar and had dimensions that coincided with those of the gel wells into which they will be loaded into for latter subjecting DNA molecules to the electrophoresis process.

B.4.—System for Fixing and Pulling Tight the Electrodes to Avoid Distortion of the Equipotential Lines in the Electrophoresis Chambers.

In the invention, it was considered that to avoid random variations of the gradient of the electric potential applied to the molecules during the electrophoresis, it is necessary that the equipotential lines in the gel were not distorted. That is achieved if the electrodes remain stretched. To attain it, in this invention, the electrodes were inserted into the chamber through the holes perforated in the floor of the CHEF chambers or in the walls of the TAFE chambers. In these holes are then inserted silicon elastics plugs, and through the plug bores are inserted the electrodes. Thus, it was warranted that even the electrodes become thinner because of the use in pulsed field gel electrophoresis, they will be pressed always by the plug and therefore fixed.

Additionally, in TAFE system the electrodes are long. So, they occasionally slacken. To avoid this problem, in this invention, the TAFE chambers were equipped with a system to pull tight the electrodes. The system has.

a rod with the top side crossed by a slot, slotted rod that is able to turn and has a waist-shaped notch which was crossed by a hole, said hole, through which an electrode end is inserted and further bended around the waist-shaped notch of the rod, a grub screw that sets the slotted rod at the desired position.

This system is placed in the chamber at the exit of the electrode. The electrodes are pulled tight by the experimenter according to the following procedure:

the grub screw, that immobilizes the slotted rod where the electrode is inserted, is loosened, the slotted rod is turned the required angle to pull tight said electrode, the grub screw is tightened to set the slotted rod in the current position and to maintain the electrode stretched.

In this way, non-distorted equipotential lines are warranted widthwise the vertical gel In this invention, reproducible patterns are warranted, because an adequate system to energize the electrodes with the proper voltage values is used, and the electrodes are maintained stretched; furthermore, systems were used to warrant that the migrations of any-sized molecules were not perturbed by local transient changes of the electrical resistance of the buffer or the gel. Such changes provoke distortions of the migration lanes and the bands formed by the molecules after the electrophoresis process.

C. Methods for Using the Chambers Provided in this Invention and Method for the Calculation and Selection of the Electrophoresis Run Time in the Chambers.

In this part of the invention, a method of calculation was created. It permits to estimate the electrophoresis running time for different electric field, temperature and duration of the electric pulses. The method is based on the existence of a set of equations that describes the migration per pulse 'm' of any lineal DNA molecule in CHEF equipments (López-Cánovas L y cols, J. of Chromatogr. A 1998, 806, 123–139). These equations are fully incorporated here as reference.

$$m = vr \cdot tp \cdot \Gamma(tp-tr) + vm \cdot (tp-tr) \cdot [1-\Gamma(tp-tr)]$$

where $$vr = 0.0207 \cdot [Q \cdot E^{1.45}/(8\pi \cdot \eta \cdot L^{1.35})];$$

$$vm = 0\ 665 \cdot [Q \cdot E^{1.76}/(8 \cdot \pi \cdot \eta \cdot L^{1.08})];$$

$$tr = 0.134 \cdot (L^{1.14}/vr)^{0.926},$$

$$\Gamma(tp-tr) = 1 \text{ if } (tp-tr) \leq 0 \text{ and } \Gamma(tp-tr) = 0 \text{ if } (tp-tr) > 0.$$

In these relationships, the variables and parameters have the following definitions 'tr' is the reorientation times (s) of a lineal DNA molecule, 'vr' and 'vm' are the migration velocities (in cm/s) of said molecule during and after the reorientation, respectively, 'Q' is the net charge of the molecule (in statcoulomb) given by 1e·bp, where 'e' is the electron charge and 'bp' the base pairs.

'L' is the contour length (in cm) of the lineal DNA molecule, given by 0.34 nm·bp.

'E' is the electric field strength in statvolt/cm,

'η' is the buffer viscosity in Poises, calculated by interpolating the value of the experimental temperature in a polynomial that relates water viscosity to the experimental temperature (in ° C.), 'tp' is the pulse time duration (s).

To feed the method, the migration per pulse 'm' of the smallest molecule is first calculated.

This is performed:

by feeding the above relations with the values of the electric field, temperature and pulse time that will be used in the electrophoresis, by feeding the above relations with the size, in base pairs 'bp' of the smallest DNA molecule to be separated, by calculating 'm', provided the electric field and temperature were comprised between 5.8 and 16 V/cm and between 10–30° C., respectively, and assuming that in the electrophoresis process were used 1.5% agarose gel and 0.5×TBE buffer (1×TBE 89 mM Tris, 89 mM, boric acid 2 mM EDTA, pH 8.3).

Once the migration per pulse is calculated, this value is used to feed the method to calculate the electrophoresis running time. In said method, the electrophoresis running time ('te' in seconds) is calculated as:

$$te=[(D/m)\cdot 2\cdot tp]$$

The method also requires the distance 'D' in centimeters that the smallest molecule is wanted to migrate in the gel. The preferred value of 'D' is the distance that separates the migration origin and the inferior edge of the gel, minus 0.1 or 0.2 cm. According to the method, for 30° C., the electrophoresis running times, needed to separate DNA molecules up to 2 Mb, are between 1.5 and 9 hours at 16 and 5.8 V/cm, respectively, whereas for 10° C., they are comprised between 2.5 and 14.5 hours at 16 and 5.8 V/cm, respectively The above mentioned steps warrant the proper use of the chamber and the obtainment of similar band patterns when equal intensities of the electric field, temperature, electrophoresis running time, buffer concentration, and electric pulses are applied The method to perform the electrophoresis process in the chambers of this invention, aided by mentioned accessories and methods, are summarized in the following steps:

- the chamber is connected to the electric field switching device, the chamber is filled with buffer solution and connected to the external heat exchanger, the proper assembly of the system to attenuate turbulences of the buffer flow is checked, and the buffer solution is circulated throughout the chamber until the desired temperature is reached,
- with the aid of the accessories to prepare gels having flat surfaces and using the proper comb, the gels are prepared for the separation of large DNA molecules, gels that are up to 0.5 cm in thickness in accordance to the selected chamber,
- into the gel wells are loaded the plugs containing the DNA molecules that will be separated, molecules that were immobilized previously in said plugs, being the plug dimensions similar to those of the gel wells,
- buffer circulation is interrupted, and the gel loaded with the plugs, is submerged in the buffer solution, which is at the desired temperature; the buffer circulation is restored
- the electrophoresis running time that will separate the DNA molecules is calculated using the calculation method that depends on the experimental conditions that will be used, as well as from the length of the gel in which the electrophoresis will be done,
- the system is energized, and the electrophoresis of the DNA molecules is performed in the gel of flat surfaces, carrying out the circulation of buffer solution at high flow velocity.

In summary, the chambers provided in this invention are small and have separations between their electrodes with opposite polarity that determine the dimensions of the chambers. Although, these electrophoresis chambers are small, they used gels that are long enough to reveal the separation of large DNA molecules in band patterns Therefore, the chambers permit high throughput sample format, fact that converts them in a new tool to perform studies that require fast results, and the comparison of the results given by numerous samples. This process can be done is short time, saving reagents and biological material.

In the following sections are shown several examples of the chambers and the accessories provided in this invention.

EXAMPLES

Example 1

Chambers that have Multiple Useful Electrophoresis Zones (UEZ): Type I TAFE Multiminichamber.

In the FIG. 1 is shown an exploded isometric view of a scheme of the chamber 1 In the view is shown the four electrodes 2 of the conventional TAFE arrangement. The width 3 of the chamber is 316 mm, the height 5 is 74 mm and the depth 6 is 114 mm. The frontal 8 and the side 9 walls of the chamber are also pointed out. The bottom 18 of the chamber has an excavation 7 that accommodates the frame 16 carrying the cast minigels 20 that the chamber uses. In the side walls 9 are the milled grooves 4 through which the frame 16 slides into the chamber. The frame dimensions are 48 mm tall by 320 mm wide by 5 mm thick. This frame supports four minigels 20 of 38 mm height and 71.25 mm width The wells 21 for loading the samples in the minigels 20 are formed by inserting a comb that has teeth of 3 mm width and spaced 2 mm.

FIG. 1 shows a three-dimensional scheme of the lid 22, of the blocks 17 that are used to occlude the non-useful electrophoresis zone (NEZ) of the chamber, and the blocks 15 that occlude the UEZ regions of the chamber.

The FIG. 2 shows the details of the side view of the chamber 1. In the side wall are marked with crosses (+) the end of the electrodes 2, being the cathodes placed in the top and the anode in the bottom. The electrodes are 316 mm length and are parallel to the frontal wall (8 in FIG. 1) of the chamber. The groove 4, for sliding the frame 16 that contains the minigels or the unframed minigels, is excavated in the middle of the side wall (9 in FIG. 1) and equidistant from the anodes or the cathodes. The blocks 17 to occlude the NEZ of the chamber, the lid 22 and the floor 18 of the chamber 22 are shown as hatched regions. The outer sides of the blocks 17 are parallels to the frontal walls 8 of the chamber, whereas the inner sides can form a small angle with the plane that contains the anode and the cathode of the same side of the gel There are blocks 17 as many as UEZ regions in the chamber Blocks 15 are used to occlude the UEZ regions.

Chamber 1 (FIG. 1) has four UEZ regions In the active UEZ regions are placed the blocks 17 (FIG. 2) to occlude the NEZ regions. To occlude the inactive UEZ regions: the blocks 17 (FIG. 2) are replaced by the blocks 15 (FIG. 2) that have rectangular shape. Minigels are not placed in the inactive UEZ regions.

To cast the minigels 20 (FIG. 1), the frame 16 (FIG. 1) is placed on a sheet made of acrylic, teflon or other suitable material, and the comb, or several single combs are inserted. Further, the agarose is poured as usually and it is covered with suitable covers To perform the electrophoresis, the sample plugs are loaded in the wells 21 of the minigels (20, FIG. 1), these minigels are introduced into the chamber (1, FIG. 1), by sliding the frame (16, FIG. 1) through the grooves (4, FIG. 1). The UEZ that will not be used are occluded with the blocks (15, FIG. 2) and in the UEZ that will be used the blocks (17, FIGS. 1 y 2) are placed. The chamber (1, FIG. 1) is filled with buffer solution and the electrodes (2, FIG. 1) are energized through the electric field switching unit by means of using a power supply. To maintain constant the temperature, cold buffer solution is circulated. The inlet and outlet tubing used for the cooling of the buffer solution are inserted in the frontal walls (8 in FIG. 1) of the chamber 1.

FIG. 3 shows the 52 band patterns 24 given by *S. cerevisiae* chromosomes in the four minigels of the chamber (1, FIG. 1). These patterns were obtained at 8.33 V/cm, 15° C., in 1.5% agarose gel, 0.5×TBE buffer solution, 12 hours of electrophoresis time and at 80 seconds of pulse time duration. The minigels were cast in the frame (16 in the FIG. 1) as it was above described.

Based on experiments done in the chamber (1, FIG. 1) in 0.5×TBE buffer solution, 15% agarose (Lachema) gel, using one, two, three or the four UEZ regions, and maintaining constant the height of the buffer in the chamber; for the equation IV was obtained $$C(vessel) = a_0 + a_1 (d/L)^{0.1}$$

where $a_0 = -0.786$ and $a_1 = 1.047$ and have variances of $1.451 \cdot 10^{-4}$ y $1\ 6949 \cdot 10^{-4}$, respectively. Both coefficients differed significantly from zero. For the equation VIII, it was additionally obtained $$Rp^{0.5} = -1.522 + Re \cdot 2.1096 \cdot 10^{-2} + 87.^{31}/V_{DC} + \text{Temperature} \cdot 2.2697 \cdot 10^{-2}$$

The coefficients of the equations were calculated by measuring '$V_{DC}$' and '$I_{DC}$' in the chambers. It permitted to estimate '$I_0$' and the maximum values of E that can be applied in MultiMiniTAFE chambers (Table 3). These results are calculated to the power supplies most used in PFGE. This procedure was used to select the dimensions of the chambers that were constructed. As it was expected, the electrolyte polarization '$I_0$' does riot linearly depend on the electric field.

For the buffer exhaustion constant, it was obtained:

$$k = -3.6365 \cdot 10^{-2} + \text{Field} \cdot 1.6135 \cdot 10^{-2}$$

On the other side, according to the equations fitted, if a power supply with a maximum output of 200 Watt and 0.4 A is used, and are also used the four UEZ of the chamber and 20° C., then, the values of 'E' near to 10 V/cm demand the replacement of the buffer solution every one hour. Thus, indicating that the use of the four UEZ regions is not efficient at said electric field values. In the example of the FIG. 3, the band patterns of the *S. cerevisiae* chromosomal DNA of the 52 samples plugs were obtained in only 12 hours, but 1 L of buffer solution had to be replaced after the first 7 hours of electrophoresis. That time coincides with the time predicted by the equations.

TABLE 3

Maximum electric field intensities ('E') that can be set in TAFE multiminichambers of different widths, using several powers supplies for PFGE.

| Power supply | Width Cm | E volt/cm T = 10° C. | E volt/cm T = 15° C. | E volt/cm T = 20° C. | E volt/cm T = 25° C. | E volt/cm T = 30° C. |
|---|---|---|---|---|---|---|
| Imax = 0.4 | 10 | 25.8 | 22.6 | 19.9 | 17.4 | 15.4 |
| Vmax = 500 | 20 | 17.4 | 15.4 | 13.5 | 11.9 | 10.6 |
| Pmax = 200 | 30 | 13.0 | 11.5 | 10.3 | 9.1 | 8.1 |
|  | 40 | 10.3 | 9.1 | 8.1 | 7.2 | 6.4 |
|  | 50 | 8.2 | 7.3 | 6.5 | 5.8 | 5.3 |
| Imax = 1.0 | 10 | 49.6 | 46.4 | 43.5 | 40.8 | 37.9 |
| Vmax = 600 | 20 | 40.6 | 37.9 | 33.5 | 29.5 | 26.0 |
| Pmax = 300 | 30 | 32.3 | 28.6 | 25.3 | 22.3 | 19.9 |
|  | 40 | 25.3 | 22.4 | 19.9 | 17.7 | 15.7 |
|  | 50 | 20.3 | 17.9 | 15.9 | 14.2 | 12.6 |
| Imax = 2.0 | 10 | 38.3 | 38.3 | 38.3 | 38.3 | 38.2 |
| Vmax = 300 | 20 | 38.3 | 38.2 | 35.8 | 33.6 | 31.7 |
| Pmax = 300 | 30 | 35.3 | 33.1 | 31.2 | 29.2 | 27.6 |
|  | 40 | 31.2 | 29.3 | 27.6 | 26.0 | 24.5 |
|  | 50 | 27.8 | 26.2 | 24.6 | 23.3 | 21.9 |

A variant of said chamber that does not use the blocks (17, FIG. 1) to occlude the NEZ can be designed. Its advantages and drawbacks are as for the chamber mentioned in the above paragraph, but the variant uses larger amount of reagents and the electric current, and consequently, the power generated in it, are higher. Nevertheless, the time required to exhaust the buffer solution is longer. Variants of these chambers can be also designed in inverted TAFE configuration. The design of the chambers that have electrodes arranged in inverted TAFE configuration is shown in the example of the type II chamber.

'E' was estimated using the equations II, III, IV y V. Imax maximum electric current output (in Ampere) of the power supply, Vmax: maximum voltage output (in volt) of the power supply, Pmax: maximum power output (in Watt) of the power supply. The values of 'E' were estimated for the 85% of Imax, Vmax and Pmax of the power supply used.

According to the above principles, it is achieved that the number of UEZ that could be activated in the chamber, the number of minigels used in an experiment, and the volume of reagents ('Bnt') used in each experiment can vary. The maximum number of sample plugs ('Nt') that can be analyzed per co-electrophoresis is also variable.

Example 2

Chambers that have Multiples Useful Electrophoresis Zones: Type II TAFE Multiminichamber.

FIGS. 4–7 show several views of a type II chamber that has 3 removable mini-platforms of electrodes.

The FIG. 4 shows a view in exploded form of a side section of the chamber 34, the removable electrode mini-platform 25, the frame 30 that supports the gel 31 and the sample plugs 36. In the mini-platform 25, the cathodes 26 are at the bottom of the chamber, whereas the anodes 27 are at the top (inverted TAFE configuration). The outer walls 28 play a role similar to the blocks 17 of the type I chambers (FIGS. 1 and 2), i e said walls eliminate the NEZ regions. In the middle of the electrode mini-platform is located the groove 29 through which is slid the frame 30 that contains the minigel 31 of the mini-platform. The pieces 40 of the mini-platforms 25 have the ducts 41 through which the tubing pass to circulate the buffer solution throughout the chamber.

It is also shown the frontal walls 33 of the chamber 34 where the mini-platforms 25 may be optionally placed. In the chamber 34, the mini-platforms walls 28 have a slot 32 to communicate the buffer solution circulating throughout the chamber. During the assembling or disassembling of the mini-platforms, the pieces 40 are slid into the grooves 35 milled in the frontal and rear walls 33 of the chamber 34.

FIG. 5 shows a top plan view of the chamber 34, which has assembled the three mini-platforms of electrodes 25.

FIG. 6 illustrates a top plan view of the chamber 34 and some details described in the above figures. In the view is schematically shown that a single electrode mini-platform 25 was assembled in the chamber. The others two regions, where the two others mini-platforms could be placed, are shown occluded with the pieces 42 constructed with a material of high dielectric constant.

FIG. 7 shows the top plant view of the lid 55, the connecting ends 43 and 45 and the electric connections 44 and 46. The cathodes (26 in FIG. 4) of the three mini-platforms are connected in parallel through the connecting ends 43 and the wires 44, while the anodes (27 in the FIG. 4) are connected in parallel through the connecting ends 45 and the wires 46. In this way, the electrodes of all mini-platforms are coupled. In this chamber, each mini-platform has its frame 30 to hold the gel 31 (FIG. 4). The sample plugs (36 in FIG. 4) are placed in the lower part of the gel, because the electrodes are arranged in inverted TAFE configuration.

To perform the electrophoresis in this chamber, first it is decided how many mini-platforms 25 (FIG. 4) will be activated, and the rest are occluded or inactivated with the pieces 42 The minigels 31 are cast in a way similar to the procedure performed in the type I chamber, and they are loaded with the sample plugs. Further, the frames containing the minigels and sample plugs are placed in the mini-platforms. Said frames can be placed in the chamber before or after the buffer solution is added. Once the process is completed, the lid is connected and the electrodes energized through the electric field switching unit connected to a power supply.

Example 3

Chambers with Single Useful Electrophoresis Zone: Minichamber CHEF.

In the FIG. 8 is shown a scheme of minichamber CHEF. Inside a hexagonal array 60 of eighteen electrodes is placed a gel 61 of agarose or other material able to polymerize and form a matrix. The gel 61 is retained in its position with the squares 62 glued to a base plate 62 that is introduced into a depression 69 excavated in the floor of the chamber Into the gel 61, are loaded the sample plugs 64 which are formed of the same material of said gel and contain immobilized chromosome-sized DNA molecules. Sample plugs 64 are loaded in such a way that, after setting the electric field at the selected intensity and switching its direction of application, the molecules are separated according to their sizes, giving as results reproducible band patterns among the different lanes of the gel. The chamber is filled with the buffer solution to permit the molecules to migrate.

The temperature, pH, concentration and others parameters of the solution should be homogeneous and constant throughout the chamber and the electrophoresis process For this reason, the buffer is exchanged continuously with an extra buffer volume that is contained in a thermostatic recipient.

To achieve buffer homogeneity, it is important to circulate said buffer solution at a high flow velocity. The buffer is added to the chamber through the inlet 65 and recovered from it through the outlet 66. In front of the inlet 65 and the outlet 66 is located a system 67 for attenuating turbulences of the buffer solution flowing throughout the chamber In the figure, are indicated the two sheets of A type 67 that were disassembled to make evident the B type sheets placed in the floor of the chamber. Turbulent flow of the solution affects the electric field homogeneity through the chamber and provokes band pattern distortion Some physical dimensions of CHEF minichambers are presented in table 4 The information does not limit the scope of this invention, but it illustrates the chambers disclosed here.

TABLE 4

Real parameters of some CHEF minichambers.

| Chamber | MiniCHEF 1 | MiniCHEF 2 | MiniCHEF 3 |
|---|---|---|---|
| Separation between electrodes with opposite polarity (cm) | 11.6 | 6.2 | 11.6 |
| Number of electrodes | 18 | 18 | 36 |
| Area of the chamber's floor (cm$^2$) including the system for attenuating the turbulence buffer flow | 272 | 94 | 272 |
| Volume of the buffer solution in the chamber (ml) | 225 | 80 | 225 |
| Dimensions of the square gel (cm) | 4 × 4 × 0.5 | 2.2 × 2.2 × 0.2 | 4 × 4 × 0.5 |
| Dimensions of the rectangular gel (cm) | 7 × 4 × 0.5 | 3.6 × 2.2 × 0.2 | 7 × 4 × 0 5 |
| Number of sample plugs of 0.15 cm width loaded into the rectangular gel | 27 | 13 | 27 |

Example 4

Chambers with Single Useful Electrophoresis Zones: TAFE Minichamber.

In FIG. 9 is shown a scheme of TAFE minichamber with an inverted electrode configuration The gel 71, which could be of agarose or other material able to polymerize to form a matrix, is placed vertically in the mid-way between the two positive electrodes 72 or the two negative electrodes 73. Sample plugs, 74 containing DNA molecules, are loaded in such a way that, after setting the electric field at the selected intensity and switching its direction of application, the molecules are separated according to their sizes, giving as results straight band patterns. The chamber is filled with the buffer solution to permit the molecules to migrate. The buffer is added to the chamber through the inlet 75 and recovered from it through the outlet 76. In front of the inlet 75 and the outlet 76 is located a system 77 for attenuating the turbulences buffer flowing throughout the chamber Some physical dimensions of TAFE minichambers are presented in table 5 The information does not limit the scope of this invention, but it illustrates the chambers disclosed here.

TABLE 5

Real parameters of some TAFE minichambers.

| Chamber | MiniTAFE 1 | MiniTAFE 2 |
|---|---|---|
| Separation between electrodes with opposite polarity (cm) | 7.8 | 10 |
| Area of the wall into which the electrodes are fixed (cm$^2$) | 127.7 | 166.8 |
| Dimensions of the chamber (cm) | 15.2 × 7.1 × 8.4 | 20.1 × 6 × 8.3 |
| Volume of the buffer solution (ml) | 530 | 800 |
| Dimensions of the gel (cm) | 7 × 4 × 0.5 | 6.3 × 5.2 × 0.4 |
| Number of sample plugs of 0.15 cm width | 27 | 24 |

Example 5

Electric Parameters of Some Minichambers of this Invention.

In this chamber, the separation between the electrodes with opposite polarity (equal or less than 15.0 cm) permits to set the electric field strengths up to 25 V/cm in TAFE and 16 V/cm in CHEF, if 0.5×TBE (1×TBE: 89 mM Tris, 89 mM boric acid, 2 mM EDTA, pH 8 3) is used and voltage less than 375.0 V is set using a power supply with a maximum output of 300 Watt. The electric resistance in these chambers is several thousand Ohm, because the small volume of buffer solution used. Because of this, high electric field strength can be achieved using a power supply with low maximum output.

The electric parameters and the power consumption of the chambers provided in this invention are shown in table 6. Measurements were done using the volumes of 0.5×TBE described in tables 4 and 5 at 20° C.

TABLE 6

Electric parameters of CHEF and TAFE minichambers.

| Chamber | MiniCHEF 1 | | MiniTAFE 1 | |
|---|---|---|---|---|
| Electric field strength (V/cm) | 10 | 16 | 8 | 20 |
| Voltage set (V) | 116.0 | 185.5 | 62.4 | 156.0 |
| Electric current intensity (mA) | 85.0 | 139.9 | 63.4 | 168.0 |
| Generated power (Watt) | 9.8 | 26.0 | 4.0 | 26.2 |

Example 6

Way of Fixing the Electrodes in CHEF and TAFE Chambers

The fixing of the electrodes in their positions in CHEF minichambers and in TAFE minichamber and TAFE multi-minichambers are shown in FIG. 10.

The electrodes are a platinum wire 81 that has an approximate diameter of 0 05 cm They communicate the electric energy from an external electric circuitry to the solution contained in the chambers, thus imposing the electric field that provokes the migration and separation of DNA molecules.

The floor 82 of CHEF chamber and the two sides walls 83 (the walls that support the gel) of TAFE chamber are bored to permit to insert into them the platinum wire forming the electrode. To fix the electrodes in the holes and avoid the leaking of the buffer solution, the wires 81 are inserted in the bore of an elastic plug 84. The elastic plug 84 should be made of a very flexible material that fit into the hole and the wire 81, even when said wire has become thinner due to the use.

Example 7

Example of a Set to Prepare Gels that Have Flat Surfaces.

A crucial element to obtain straight and reproducible band patterns using these chambers is the shape of the gels 61 and 71. The surfaces of said gels should be flat, otherwise the homogeneity of the electric field in the gel will be affected and distorted band patterns will be obtained. A rear view of the accessories used to cast the gels 61 and 71 is shown in FIG. 11.

Gels 61 and 71 are cast on a base plate 91 of flat surfaces, which is large enough to support the frame 92. The frame thickness 92 will determine the gel thickness that will be cast. The dimensions of the internal cavity of flat surfaces 93 will determine the width and the length of the gels 61 and 71.

In the outer sides of the frame 92, are the notches 94. They are near to an edge of the frame 92 and evenly separated from such edge. The legs 96 of the comb 95 will be fitted into the notches 94, then the notches 94 are as wide as the legs 96.

The comb 95, has teeth 97 with bevel cuts to make equal their cross-sections to those of the sample plugs 64 and 74. The comb 95 is flat in the frontal part whereas in the rear over the teeth 97 it gains thickness forming a step, being the length of the teeth equal to the frame thickness 92 minus 1.0 mm. The legs 96 are of this length. In FIG. 11 is shown the magnification of one of the teeth 97 to appreciate the step.

The cover 100 has flat surfaces and one of its edges has a bevel cut in wedge formation 101. A magnified view of part of the bevel edge 101 is shown. The width of the cover 100, at least in the bevel edge 101, is larger that the width of the cavity 93 of the frame 92 The cover 103 also has flat surfaces, excepting the edge that has the protruding end 104 of 0.1 cm thickness. A magnified view of part of the protruding end 104 is shown. The protruding end 104 is wider than the cavity 93 of the frame 92, but it is shorter than the distance between the internal faces of the legs 96. The comb 105 is similar to the one 95, but its teeth 106 are 0.2 cm shorter.

To cast the gel, the base plate 91 is placed on a horizontal surface, the frame 92 is placed on said surface, with the notches near the back of the base plate 91. The comb 95 is fitted into the notches 94 with the teeth 97 turned forward. After that, the cover 100 is placed on the frame 92 in front of the comb 95 with the flat surface turned to face the frame and the bevel edge 101 against the comb. The arrows indicate the direction of accessories assembly The accessory set is immobilized by fixing with clamps, or other device, the frame 92 to the base plate 91. The agarose or other solution able to polymerize is poured behind the comb 95. The temperature of the molten agarose is from 65 to 70° C. For other solution the temperature can vary. The volume of molten gel, to be added, should be enough to fill to the brim of the cavity formed among the base plate 91, the walls of the cavity 93 of the frame 92 and the cover 100. Further, the cover 103 is placed on the frame turning the flat face downward and the protruding end 104 against the back of the comb 105. It removes the remaining molten gel. The assembled accessory set is left to set until the molten gel solidifies.

After the gel 61 or 71 was cast, the comb 95 is removed and the sample plugs 64 or 74 are loaded in the wells 107 which were formed after removing the comb. As the cross-sections of the teeth 97 and the sample plugs 64 and 74 are equal, the sample plugs are uniformly loaded widthwise the gel and evenly separated from the edges of said gel 61 or 71. When the sample plugs 64 and 74 were already loaded, they are further pushed into the gel 61 or 71 with the aid of the comb 105 to place all plugs at similar depth.

The suitable use of the accessories described in this invention permits to cast gels of flat surfaces and the alignment of the sample plugs containing immobilized DNA molecules This is one of the necessary conditions to obtain straight and reproducible band patterns Example 8

Gel of the CHEF Minichambers and Placement of them in the Minichambers

Gels of different sizes can be placed in CHEF minichambers. To retain the gel 61 (FIG. 12) in a given position during the electrophoresis, a plastic or acrylic rectangular base plate 63 is used. Square flanges 62, are placed on the base plate 63. Each square flange 63 is placed at each corner of a rectangular or square contour where the gel 61 will be retained. The separations between the square flanges 62 are as the same dimensions (length and width) of the gel 61 that will be placed on said contour. The maximum height of the square flange 62 should be 0.2 cm, to avoid the attenuation and distortion of the electric field generated in the chamber The base plate 63 is inserted into the floor of the chamber in the center of the electrodes 60 array In this region of the chamber, there is an excavation 69 with a rectangular shape of dimensions as those of the base plate 63. The depth of the depression 69 is equal to the thickness of the base plate 63, then the gel 61 will be retained at the same level of the chamber floor. The base plate 63 has several notches in the edges and in the corners to facilitate its extraction from the excavation when the experiment is finished. Excepting for the position of the square flanges 62, all the base plates 63 are identical. Then, gels 61 of different sizes can be used in the same chamber. It is important that the set warrants that the gel 61 is well positioned during the electrophoresis to obtain straight and reproducible band patterns.

To perform the electrophoresis, the gel 61 loaded with the sample plugs 64 that contains the DNA molecules (said gel prepared with the accessories described in the example 7). is taken and placed on the base plate 63 between the four square flanges 62. After that, the base plate 63 holding the gel 61 is inserted into the excavation 69 of the floor of the chamber. Because DNA molecules acquire negative charge in solution at neutral pH, they migrate toward the anodes, then, the base plate 63 should be placed with the sample plugs 64 nearer to the cathode. When the electrophoresis ends, the gel 61 is removed from the chamber to stain the DNA molecules and visualize the band patterns To clean the chamber or use a different sized gel 61, the base plate 63 is removed by inserting a bar into the notches 111 and levering the base plate 63.

Example 9

System to Pull Tight the Electrodes of the TAFE Minichambers

The electrodes of TAFE minichambers are slacken as they are used. In the FIG. 13 is shown a device to pull tight the platinum wires 81 that form the electrodes. The slotted rod 115 has a waist-shaped notch 116 crossed with a hole 117 that has a diameter slightly larger than the platinum wire 81. The wire end 81 is inserted into the hole 117 and the slotted rod 115 is turned with a screwdriver placed in the slot 118 until the wire 81 is pulled tight. To fix the position of the slotted rod 115 a grub screw 119 is loosened before the wire 81 is pulled tight and then the grub screw is tightened again.

Example 10

System for Attenuating Turbulences of the Buffer Flowing Throughout the CHEF Minichambers CHEF minichambers have a system to attenuate turbulences of the buffer flowing throughout the chamber, thus permitting the circulation of the buffer at high flow velocities. In the FIG. 14 is shown a scheme of the system to attenuate turbulences of the buffer flowing throughout the CHEF chambers. It is formed by impermeable A type sheets 121 and B type sheets 122 that are made of a material with high constant dielectric to avoid perturbations of the applied electric field.

The type A sheets 121 are the tallest, and are placed separated from the floor of the chamber to avoid the buffer to overflow them and forcing the solution to flows under them The B type sheets 122 are the shortest, they are glued to the chamber and surpass the gap formed between A type sheets 121 and the floor of the chamber.

The A type 121 and B type 122 sheets are placed alternately, beginning and ending with A type sheets 121 and placing between them B type sheets 122. The set of A 121 and B type 122 sheets are placed in front of the inlet 65 and outlet 66. The pairs of A 121 and B type 122 sheets can be repeated as many as times as desired until the last is 1 0 cm apart from the electrodes.

The buffer solution is injected through the inlet 65 and flows alternately under A type sheets 121 and over the B type 122. This biased trajectory (pointed out by the arrows) will attenuate the variations of the fluid pressure provoked by the injection, when the buffer flows over the gel 61, it almost runs at constant velocity with the absence of turbulent flow The same process takes place in the other side of the chamber, from which the solution is recovered through the outlet 66.

Example 11

System for Attenuating Turbulences of the Buffer Flowing Throughout the TAFE Chambers.

The TAFE chambers that have single or multiple UEZ also have a system to attenuate the turbulences of the buffer flowing throughout the chamber, thus permitting the circulation of the buffer at high flow velocity.

In the FIG. 15 is shown a detailed scheme of the system to attenuate the turbulences of the buffer flowing throughout a TAFE minichamber with a single UEZ.

The system is made of impermeable sheets 131 with high dielectric constant. They avoid the free buffer flow throughout the chamber, excepting through the slots 132. The buffer solution is injected through the inlet 75 and it is discharged through the outlet 76. The fluid pressure changes produced during the injection and discharge of the buffer from the chamber are attenuated in the cavities 133, so when the buffer flows through the gel 71, it almost runs at constant velocity with the absence of turbulent flow. The arrows indicate the trajectory of the buffer from inlet 75 to the outlet 76

The maximum velocity of flow in these chambers that does not provoke turbulent flow of the buffer depends on the size and the volume of the chambers. The maximum flow velocities that could be used in the chambers disclosed in examples 3 and 4, and do not perturb the solution are shown in table 7

TABLE 7

Maximum flow of circulation that does not provokes turbulent flow of the buffer solution filling PFGE minichambers.

| Chamber | Volume (ml) | Maximum flow velocity with Buffer exchange time the absence of turbulent flow (minutes). (ml/minute). | |
|---|---|---|---|
| MiniCHEF 1 | 225 | 100 | 2.25 |
| MiniTAFE 1 | 530 | 280 | 1.89 |
| MiniCHEF 2 | 80 | 44 | 1.82 |

Buffer exchange time refers to the time that has to elapse until one chamber volume of buffer must be exchanged.

Example 12

Accessory Set to Prepare the Sample Plugs

As above stated, to obtain reproducible band patterns it is essential to have samples plugs with identical shape, dimensions and DNA concentration. Said sample plugs must have dimensions and shapes similar to those of the wells of the electrophoresis gel.

In the FIG. 16, is shown one of the accessory sets designed to obtain sample plugs with said characteristics. Such set has the sample plug applicator 141, the sample plug handler 142, the sample plugs maker 143, its cover 144 and the sample plug cutter 145.

In the example, the sample plugs maker 143 is an acrylic, rubber or silicon rectangular block (7×6.9×1 cm length× width×depth) with smooth and flat surfaces, excepting one of said surfaces that has eleven parallel and rectangular grooves 146 excavated on it Said grooves are spaced widthwise of the block in such a way, that the width of the groove coincides to the height of the sample plugs 148 and the depth of the groove 146 coincides to the thickness of the sample plugs 148.

The cover 144 is a glass or acrylic rigid and flat sheet that is placed on the grooved surface of the sample plug maker 143. Pieces 143 and 144 are kept together to warrant the airtightness between the different grooves 146. Using a pipette an agarose cell suspension is dispensed into each end of the said grooves. The grooves are well filled and the set is left to set until the agarose solidify. To remove the cover 144, said cover is slid transversally to the grooves 146, in order to avoid the dragging of the solidified agarose strips 147. The strips 147 are cut in small sample plugs 148 with the cutter 145. To do it, the cutting edge of the protuberances 149 are placed on each groove and pressed downward to the bottom side of each groove 146. The distance between the protuberances of the sample plugs cutter determines the width of the sample plugs 148, so it is warrant that the sample plugs 148, containing the DNA molecules, have the same shape and dimensions.

Once the samples plugs 148 were cut, the sample plug applicator 141 is used to drag said sample plugs through the grooves 146 and then, to let them fall into the vessels containing the solutions to treat the cells. The sample plug applicator 141 is also used to load the sample plugs 148 into the wells 107 (FIG. 11) of the electrophoresis gel. The sample plug handler 142 is used to recover the sample plugs from the vessel where the sample plugs are treated or stored.

Example 13

*Saccharomyces cerevisiae* Chromosomes Band Patterns Obtained in TAFE Minichamber (With a Single UEZ)

In the FIG. 17 is shown an example of an electrophoresis done in a TAFE minichamber that has 7.8 cm of separation between the electrodes with opposite polarity This minichamber uses a gel 151 that is 7.0 cm width and 4.0 cm length. In the gel 151, thirteen sample plugs 152 were loaded, which were 0.25 cm width, 0.07 cm thick and 0 2 cm depth. *Saccharomyces cerevisiae* intact chromosomal DNA contained in the sample plugs 152 were separated during the electrophoresis in the band patterns 153 in each lane of the gel 154. Each band pattern has eleven bands. The running conditions were 60.0 seconds of pulse time, 7.0 hours of electrophoresis, 1.5% agarose, 0.5×TBE, 20° C. and 10.0 V/cm. Gel staining was performed with ethidium bromide.

The above results indicate that TAFE minichamber give a rapid and adequate separation between the bands of the patterns, as well as reproducible patterns between the lanes of the gel.

Example 14

Reproducibility of the Band Patterns Obtained in CHEF Minichambers

The results of three electrophoresis runs done in a CHEF minichamber that has 11.6 cm of separation between the electrodes with opposite polarity are shown in the FIG. 18. That minichamber uses square gels 161, 162 y 163 of 4.0 cm width. Into the gels 161, 162 and 163 seven sample plugs 164, 165 and 166 of 0.25 cm width, 0 07 cm thickness and 0 2 cm depth were loaded. *Saccharomyces cerevisiae* intact chromosomal DNA, contained in the sample plugs 164, 165 and 166, were separated during the electrophoresis in the band patterns 168, 169 and 170 in the lanes 171, 172 and 173 of the three gels 161, 162 and 163. The running conditions were 50.0 seconds of pulse time, 3.5 hours of electrophoresis, 1.5% agarose, 0.5×TBE, 20° C. and 9.82 V/cm. Gel staining was performed with ethidium bromide.

In the figure, it can be observed that the patterns obtained in the gels 161, 162 and 163 have the same number of bands in all lanes. Besides, each band 168, 169 and 170 migrated the same distance in the seven lanes 171, 172 and 173 of any of the gels 161, 162 and 163. On the other hand, in each lane 171, 172 and 173 of the three gels 161, 162 and 163, the same electrophoresis band pattern is observed. Said band patterns have the same number of bands 168, 169 and 170, indicating that the minichamber gave reproducible results in different experiments in very short times (3.5 hours)

BRIEF DESCRIPTION OF DRAWINGS

FIG. 1 is an exploded view of the three-dimensional scheme of a type I TAFE chamber that has its electrode array in conventional TAFE configuration, the grooves through which the gel frame, supporting all minigels and the samples of the four UEZ of the chamber, is slid. Three-dimensional schemes of the frame, minigels, and the cover carrying the blocks that eliminate NEZ or UEZ regions are also shown.

FIG. 2 is a side view of a scheme of a type I TAFE chamber. The blocks that eliminate the NEZ, the electrode array in conventional TAFE configuration, and the blocks that occlude the UEZ that are not going to be used in the electrophoresis are shown FIG. 3 shows the electrophoresis band patterns given by *S. cerevisiae* chromosomes when they were separated in the four minigels used in the type I TAFE chamber of the FIG. 1. The molecules were separated at 8.33 V/cm, 15° C., during 12 hour of electrophoresis in 1.5% agarose gel, 0.5×TBE buffer solution and at 80 seconds of electric pulse duration. After 7 hours of electrophoresis, one liter of buffer solution was replaced.

FIG. 4 is an exploded view of a side section of the type II TAFE chamber. One of its miniplatforms of electrodes arranged in inverted TAFE configuration, its gel frame and its gel, as well as the placement of the samples in the bottom of the gel are shown. The electrode miniplatforms are removable.

FIG. 5 is a plant view of a scheme of the chamber that has 3 miniplatforms of electrodes. The three miniplatforms were placed in the chamber.

FIG. 6 is a plant view of a scheme of the chamber that has three miniplatforms of electrodes. One miniplatform was placed in the chamber and the others were occluded using pieces of the proper shape and material.

FIG. 7 is a plant view of a scheme of the chamber lid. The electrical connections are shown

ADVANTAGES OF THE PROPOSED SOLUTIONS

Figure 1:
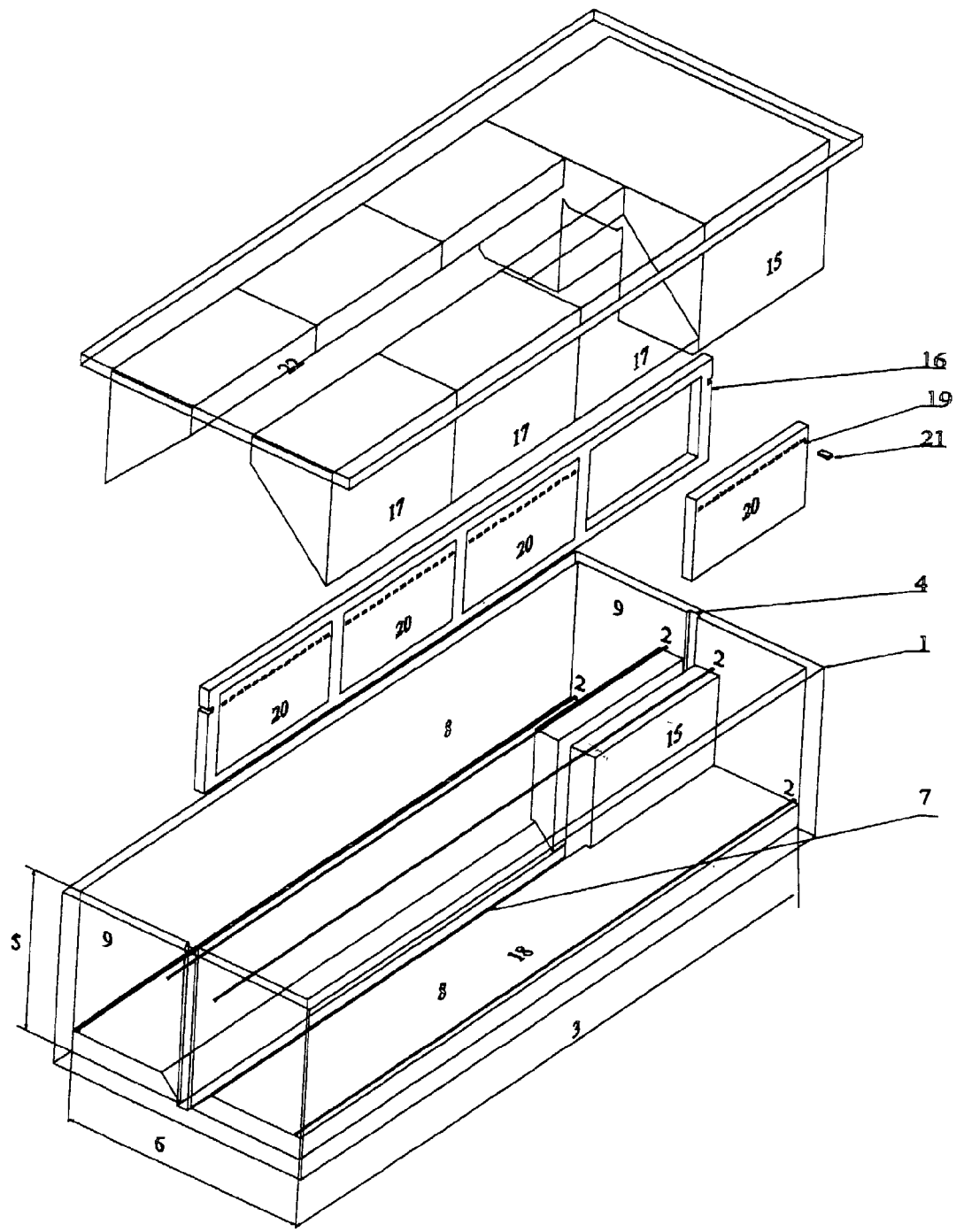
FIGS. 1 to 3 are schematic diagrams of type I TAFE chambers and electrophoresis patterns.
Figure 2:
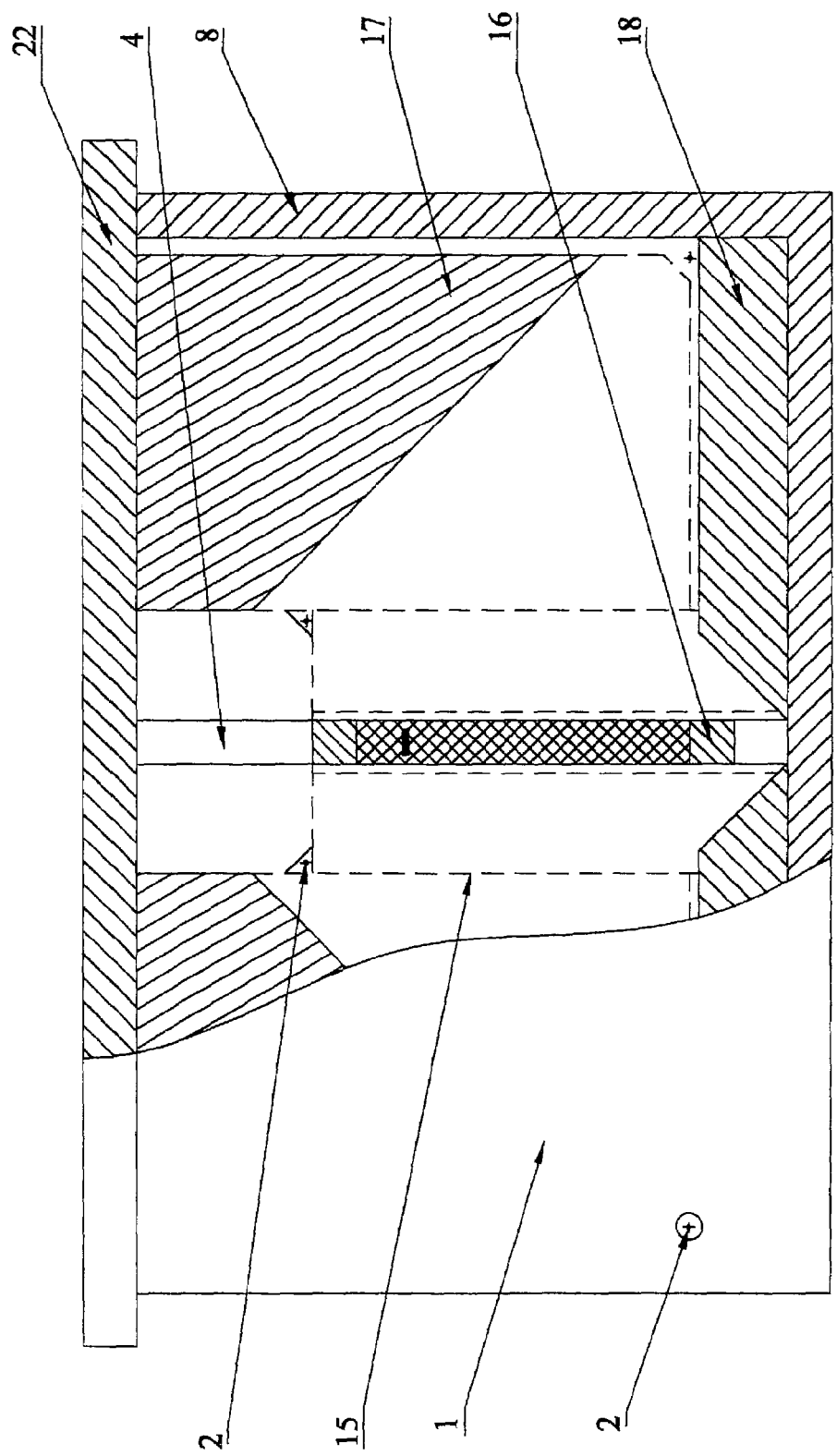
Figure 3:
Figure 4:
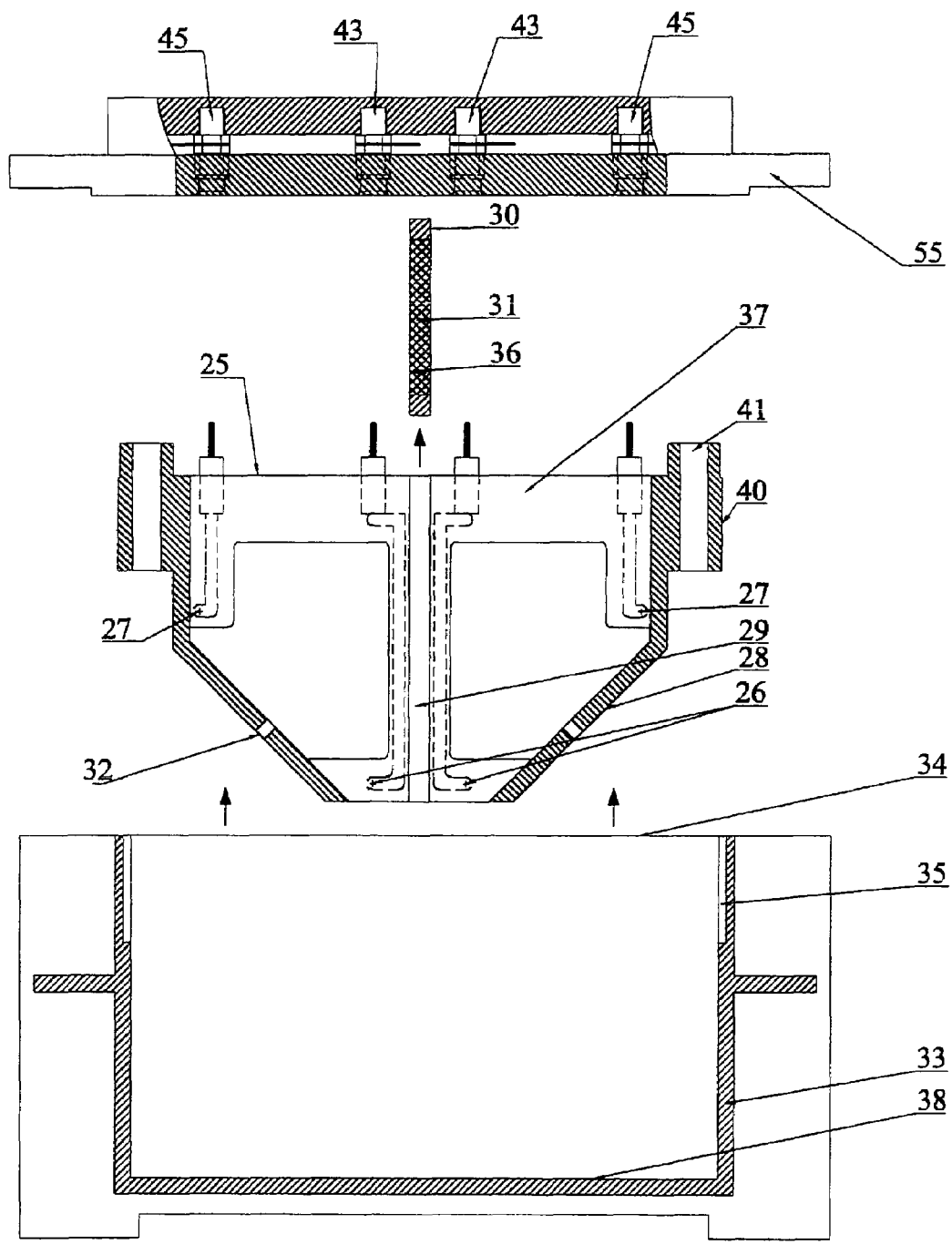
FIGS. 4 to 7 are schemes of the distinguishing features of the type II TAFE chambers
Figure 5:
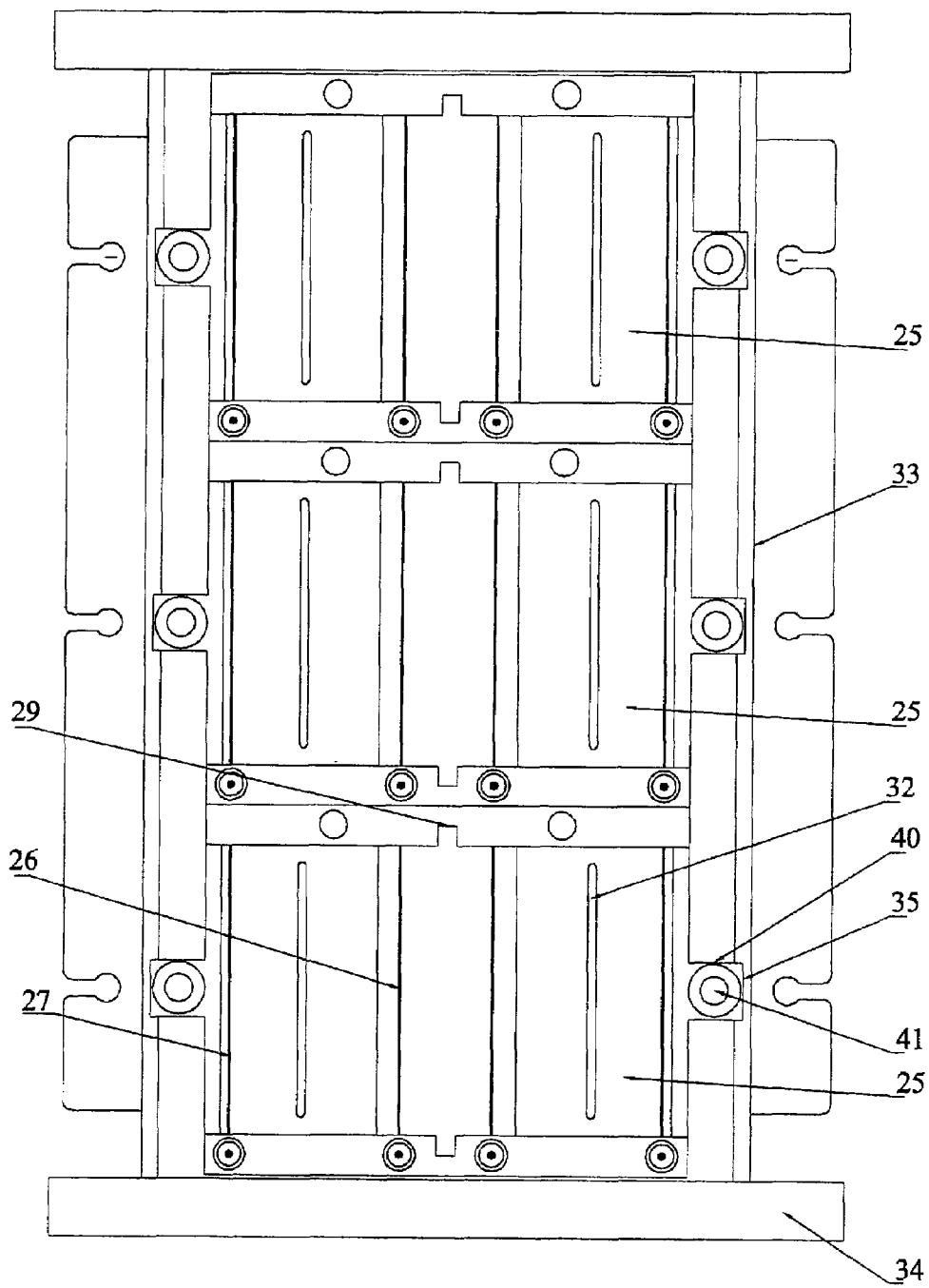
Figure 6:
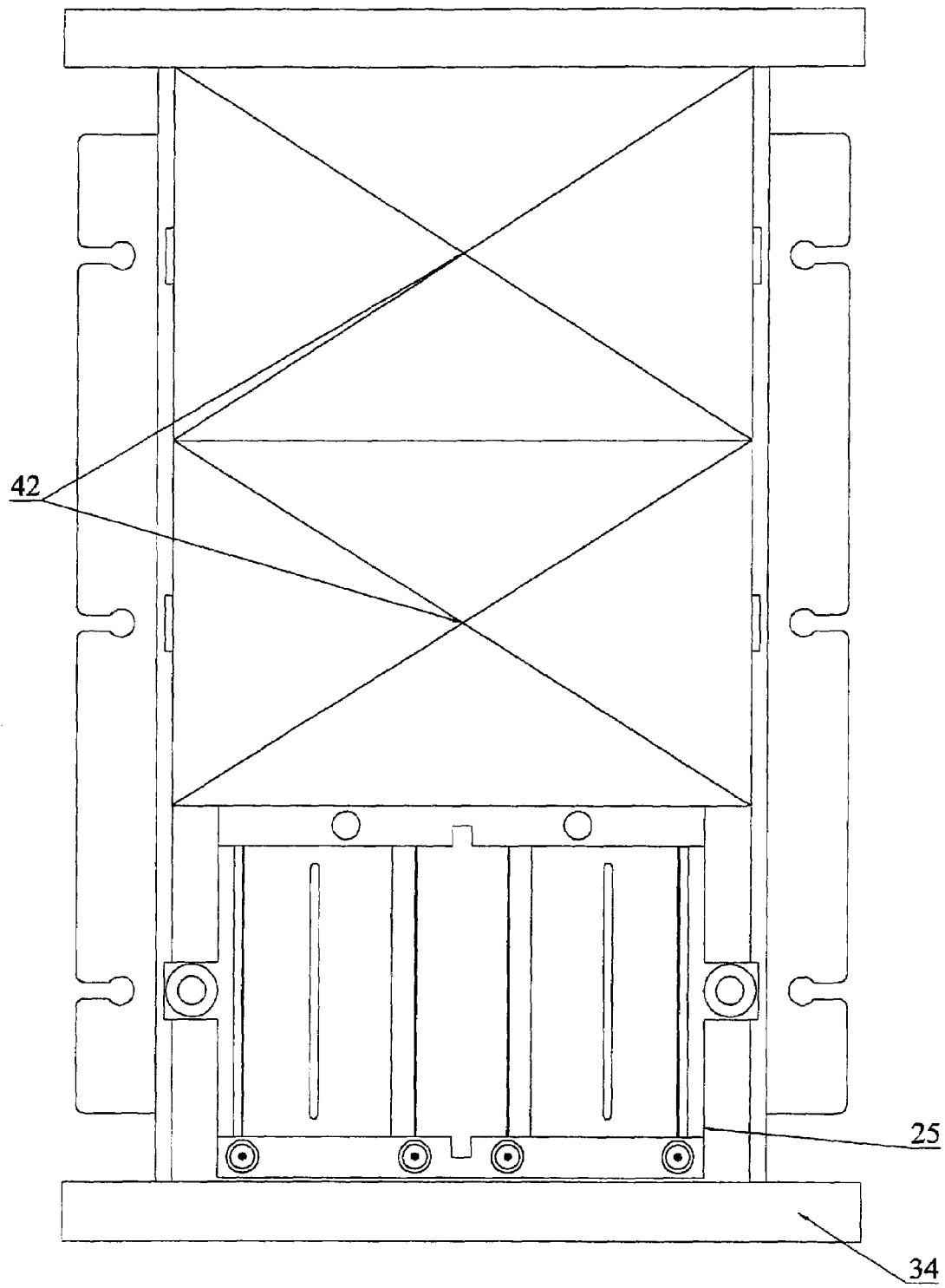
Figure 7:
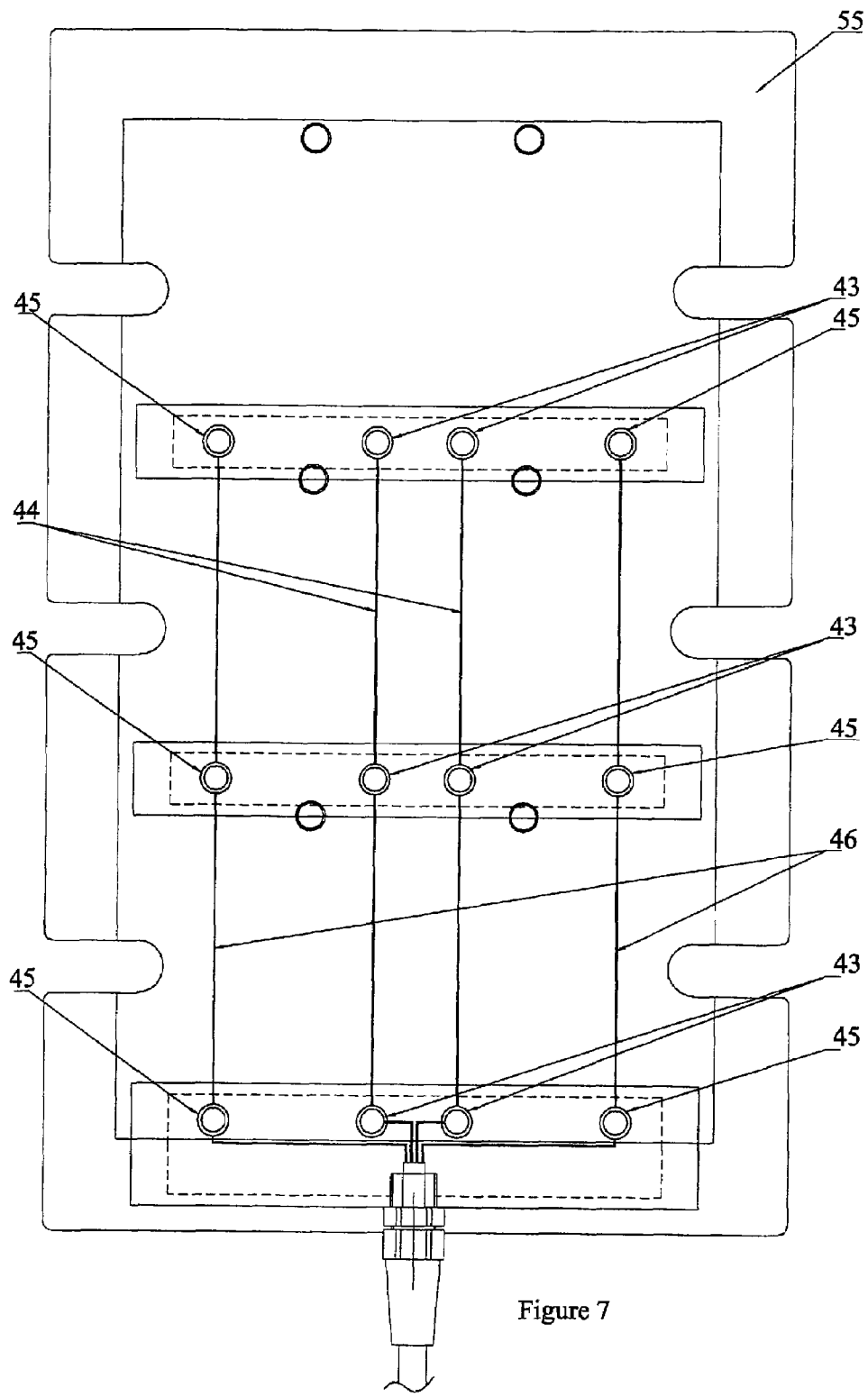
Figure 8:
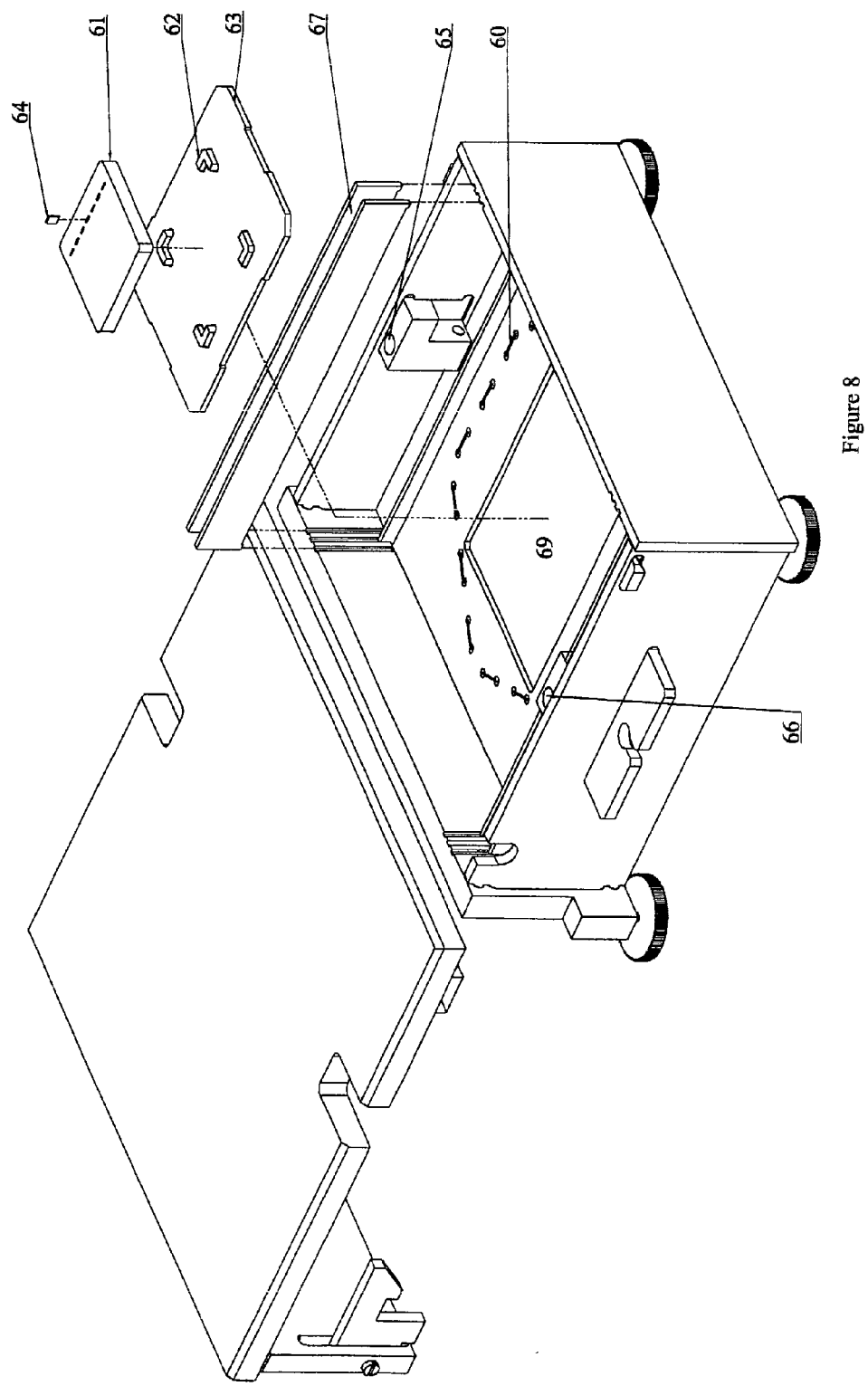
FIG. 8 is an exploded isometric view of a scheme of a CHEF minichamber The chamber, its electrode array and the lid of said chamber are shown. The base plate and the flanges of the square gel are also shown, as well as the gel and a hypothetic sample plug. The A type sheets of the system for attenuating turbulences of the buffer solution flowing throughout the chamber are shown disassembled. In the floor of the chamber is appreciated the B type sheet.
Figure 9:
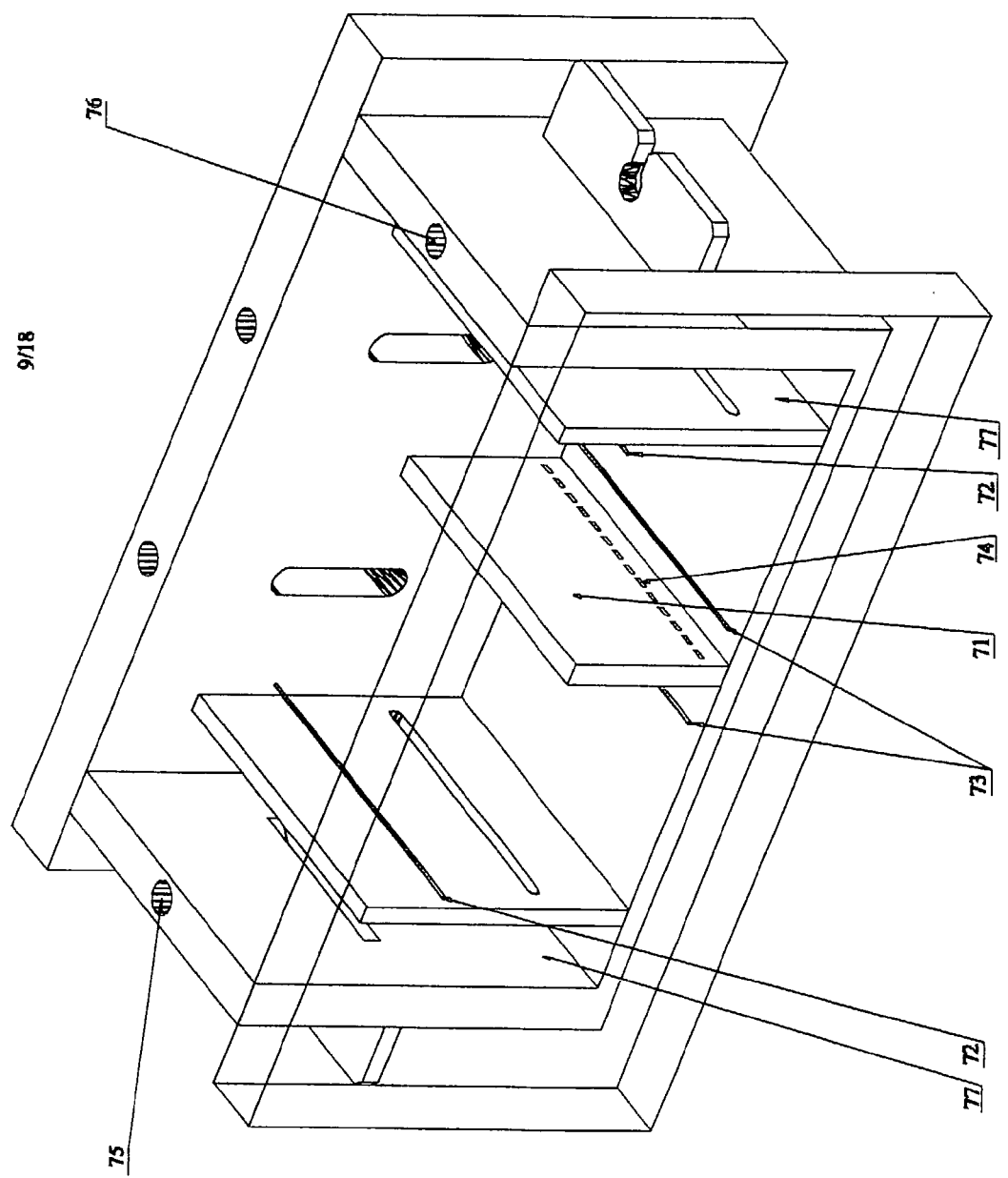
FIG. 9 is an isometric view of a scheme of a TAFE minichamber that has the electrodes arranged in inverted TAFE configuration. In the figure, the frontal wall of the chamber was drawn transparent to reveal the details inside the chamber. In the center of the chamber is observed the gel surrounded by the four electrodes. Beside the electrodes are shown the slotted sheets of the system for attenuating turbulences of the buffer solution flowing throughout the chamber.
Figure 10:
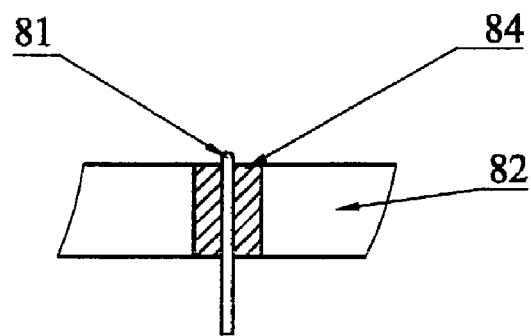
FIG. 10 shows the way to fix the electrodes in the walls of TAFE minichambers or in the floor of CHEF minichambers. In the upper part, a cross section view of a region of the CHEF floor is shown, whereas a region of the TAFE wall is shown in the lower part of the figure. The electrodes inserted into the bore of the silicone plugs are also shown
Figure 10:
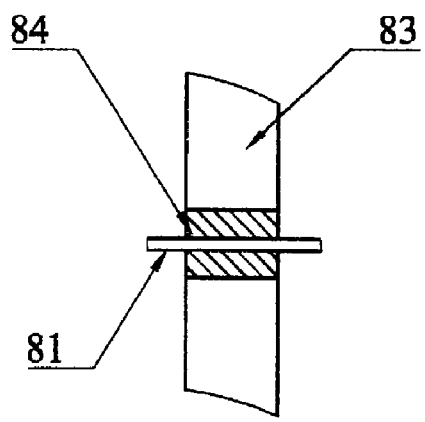
Figure 11:
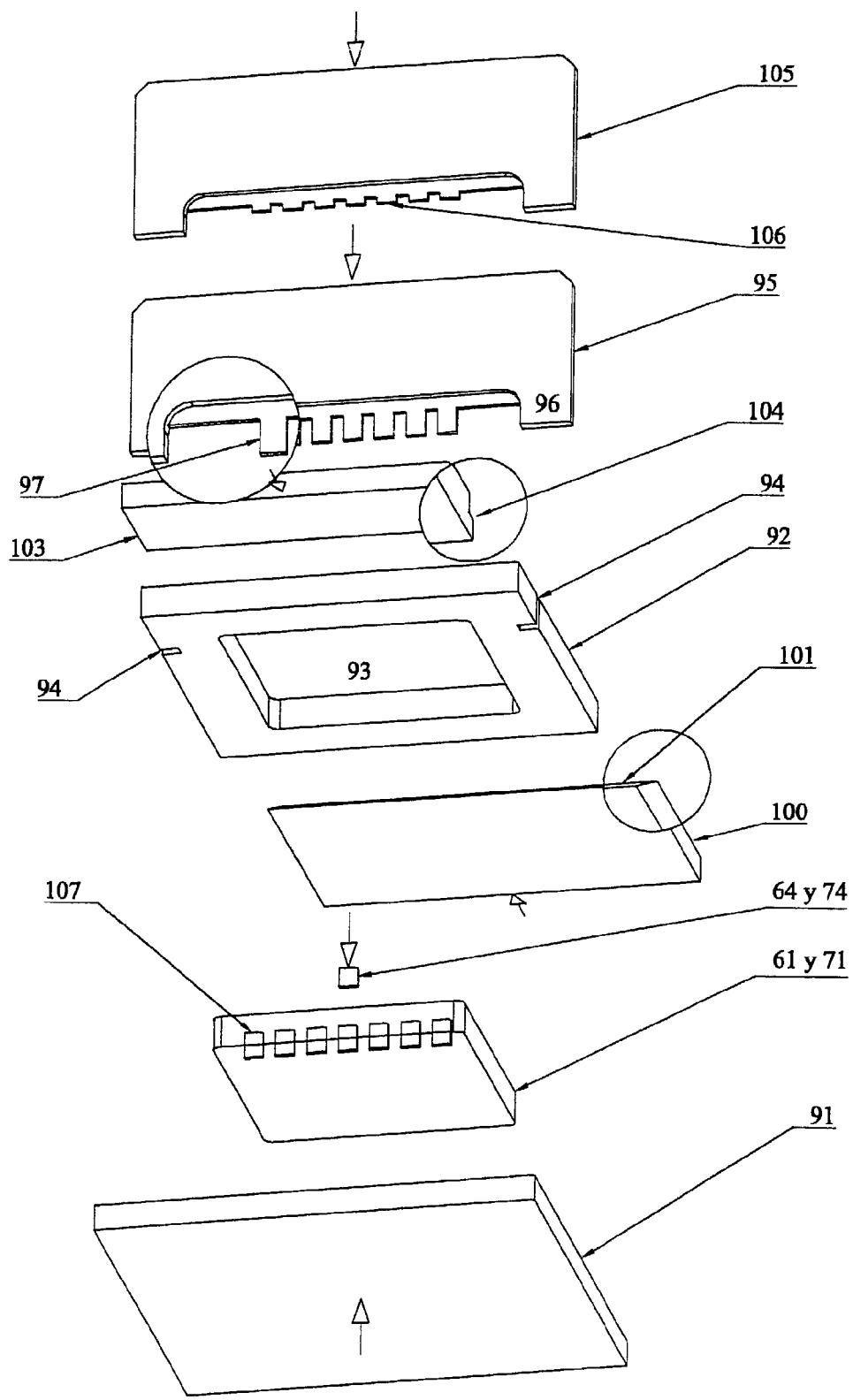
FIG. 11 is a rear view of a scheme of the accessory set to cast gels with flat surfaces as well as the comb to align the plugs in the gel. In the lower part of the figure is observed the base plate to cast the gel, above it is a gel scheme with its wells and a hypothetical sample plug. Above the gel are the frontal cover of the frame, the frame and its notches, and the rear cover of the frame. In the upper part of the figure, are shown schemes of a comb to form the gel wells and the comb to align the sample plugs in the gel. Arrows indicate the direction of the accessories assembling.
Figure 12:
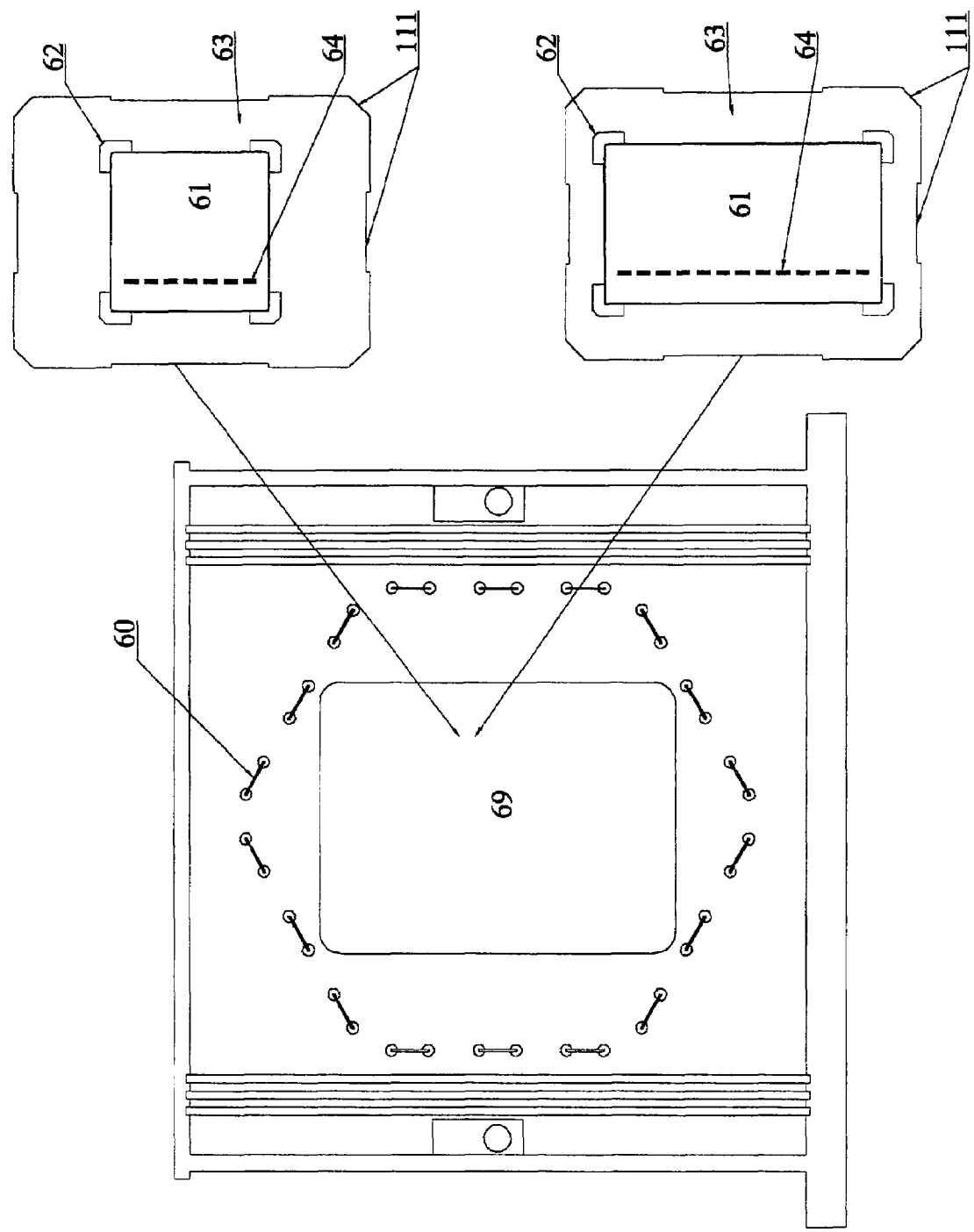
FIG. 12 shows in the left upper part, a scheme of the base plate carrying the square gel In the right upper part, the base plate carrying the rectangular gel is shown. In the lower part, a top view of the scheme of the CHEF minichambers is shown. Here, are also shown the hexagonal electrode array and the excavation where the base plates carrying the gels are placed.
Figure 13:
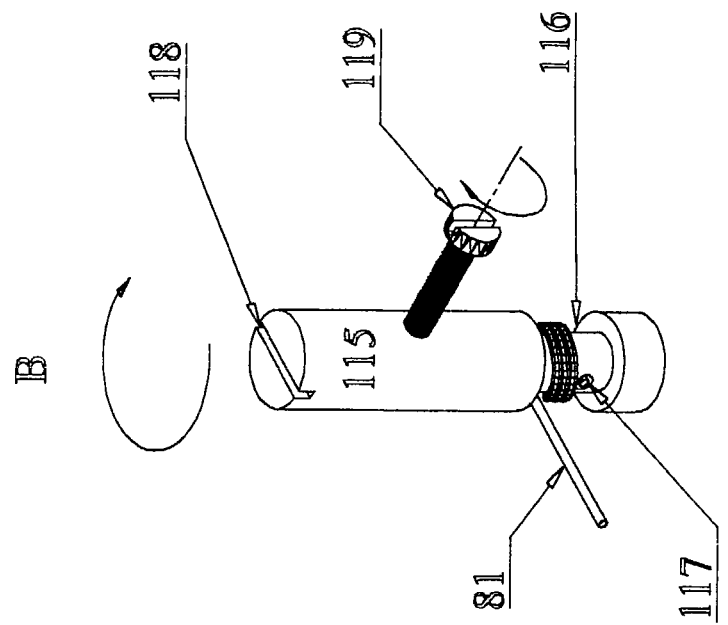
FIG. 13 shows a scheme of the device to pull tight the electrodes of TAFE minichambers. In the left part (A) is shown the slotted rod having loosened the grub screw as well as the platinum wire end at the entry of the slotted rod hole. The arrows indicate the direction for pieces assembling. In the right part (B) is shown the slotted rod with the electrode end inserted into it and coiled around its waist, the slotted rod already rotated, and the grub screw tightened.
Figure 13:
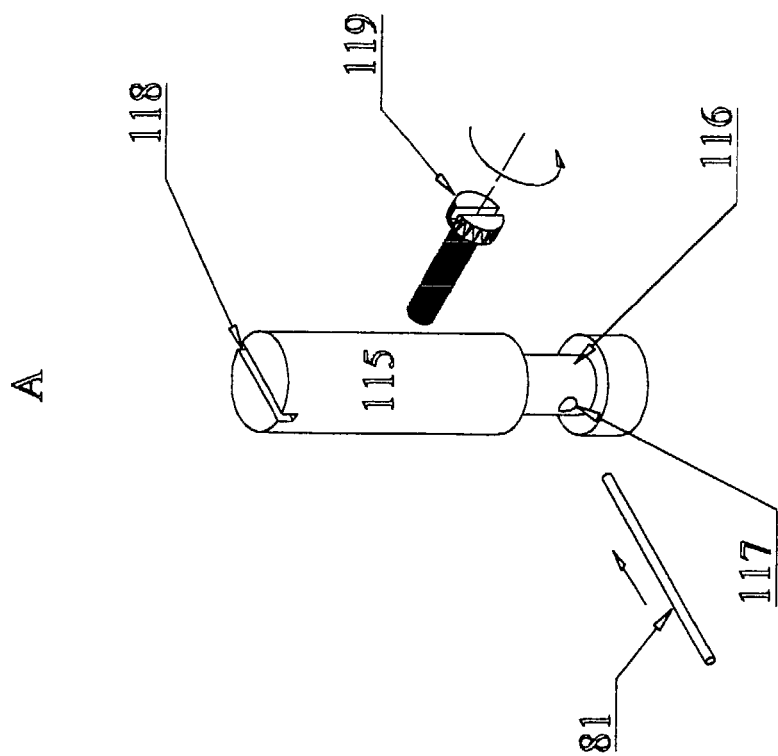
Figure 14:
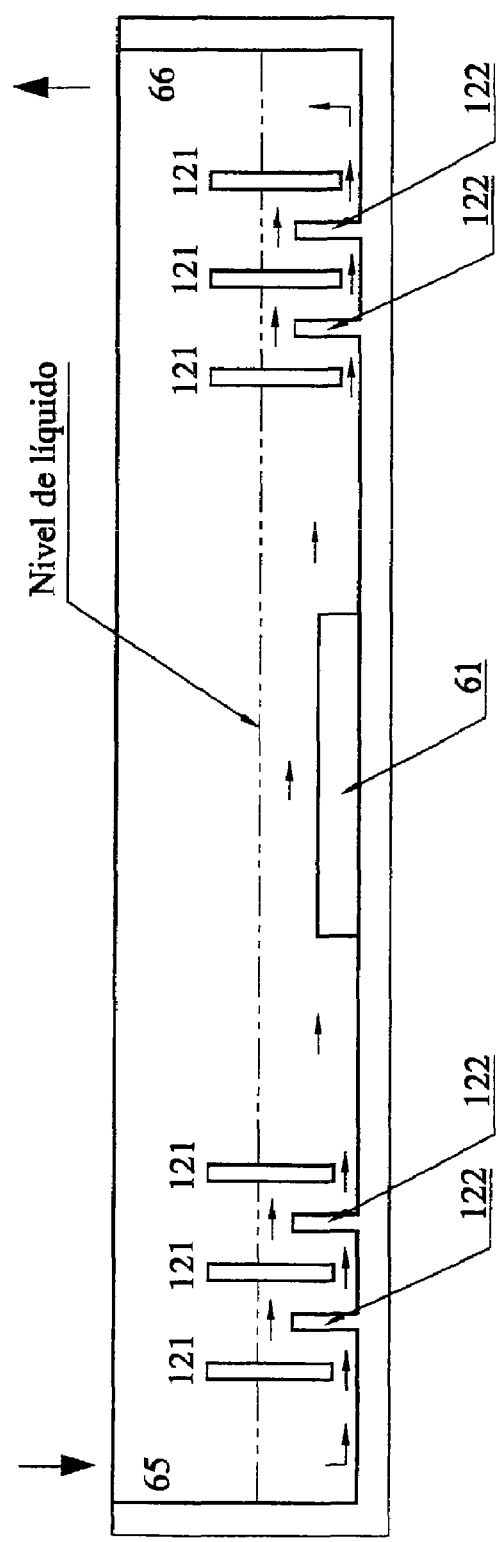
FIG. 14 is a side view of a scheme of the system for attenuating turbulences of the buffer solution flowing through CHEF minichambers, in which the wall was drawn transparent The horizontal gel is observed in the middle of the figure. Immediately, at both sides of the gel are placed alternately the A and B type sheets. The arrows indicate the flowing of buffer solution throughout the electrophoresis chamber.
Figure 15:
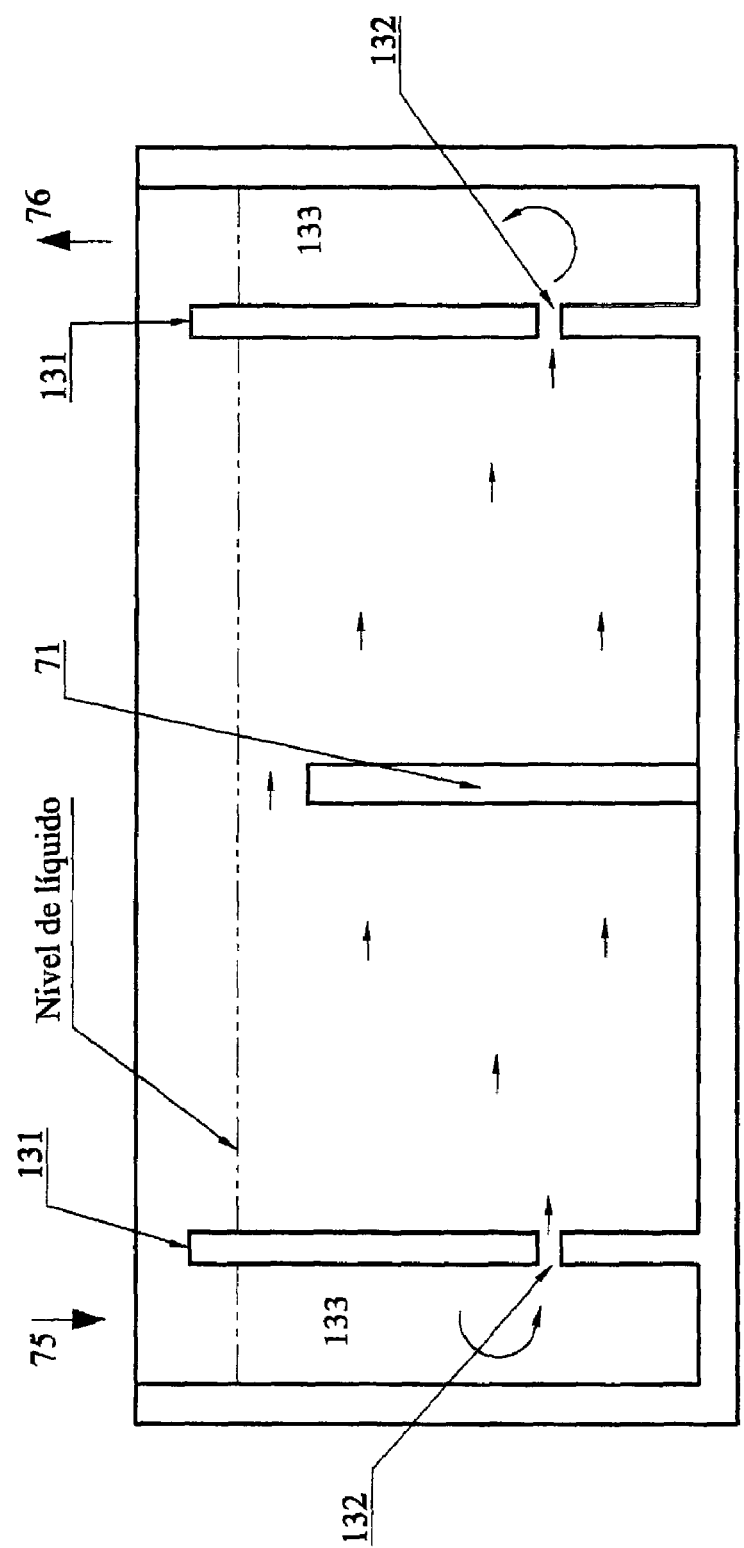
FIG. 15 is a side view of a scheme of the system for attenuating turbulences of the buffer solution flowing throughout TAFE minichambers, in which the wall was drawn transparent. The vertical gel is observed in the middle of the figure. At both sides of the gel are the sheets of said attenuation system. The arrows indicate the flow of the buffer solution throughout the electrophoresis chamber.
Figure 16:
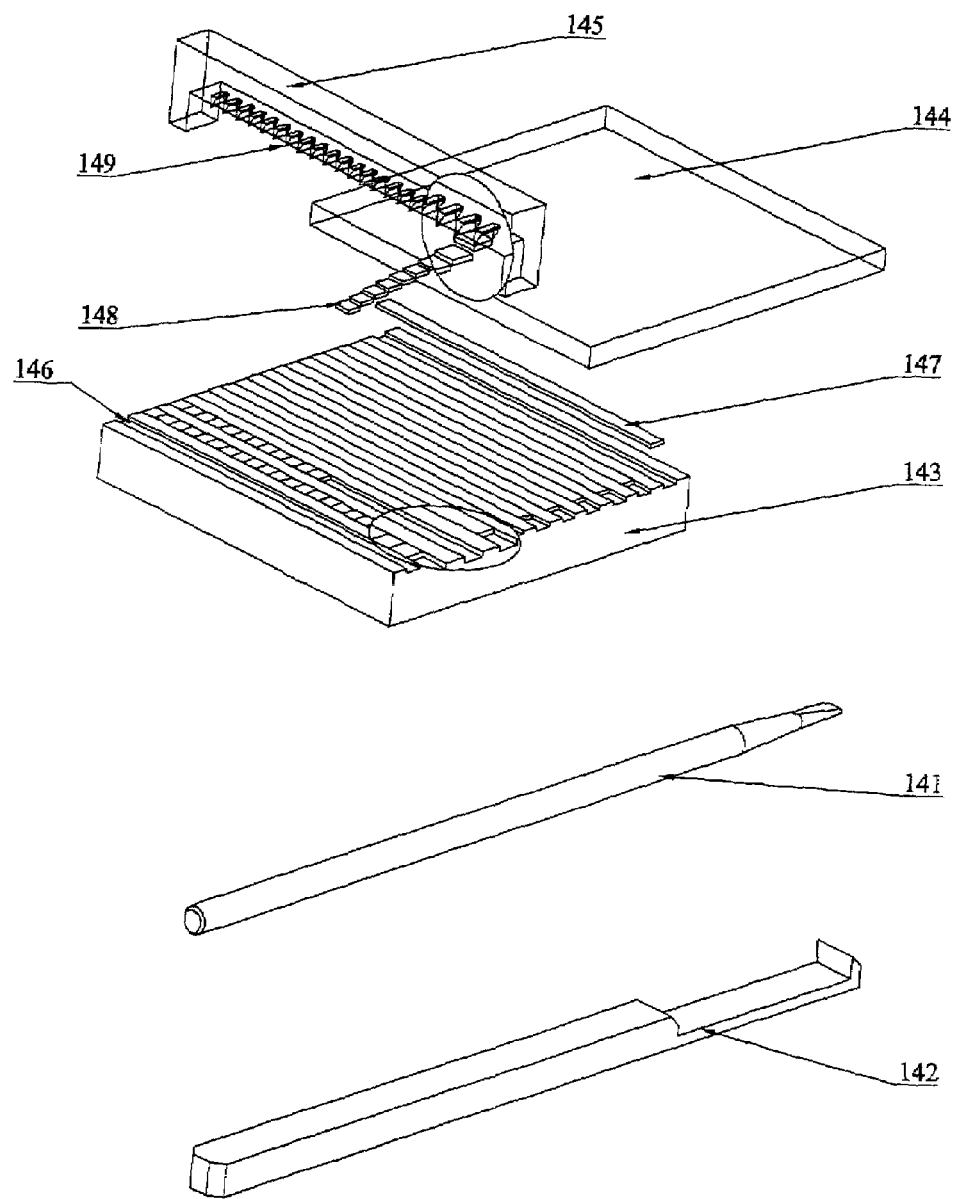
FIG. 16 shows a scheme of the accessory set to form homogeneously sized sample plugs containing immobilized DNA. In the lower part of the figure is presented the sample plug handler, and immediately above it, the sample plug applicator. Above them is the block of the sample plug maker displaying its lengthwise grooves, and are several strips of solidified agarose that were already cut to form plugs. Intact strips of solidified agarose are also shown. The cover of the block is shown above. In the upper part of the figure are presented the sample plug cutter and several plugs that were already cut.
Figure 17:
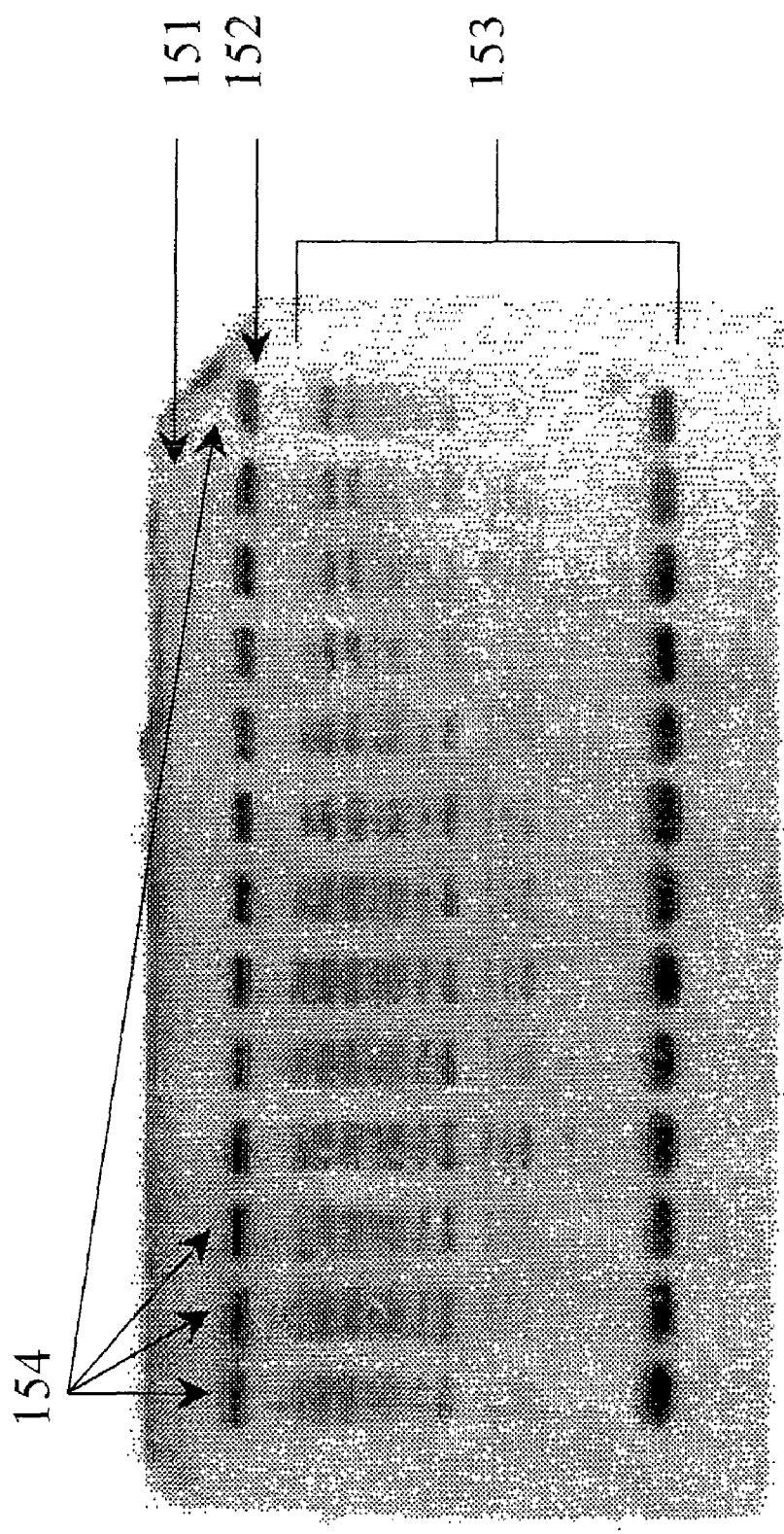
FIG. 17 shows the electrophoresis patterns obtained in a TAFE minichamber. The chromosomes of intact DNA samples from *Saccharomyces cerevisiae* were separated, they were previously immobilized in thirteen agarose plugs. Electrophoresis conditions, 60 of pulse time, seven hours of electrophoresis, 1.5% agarose, 0.5×TBE, 20° C., 10 0 V/cm. The gel is 4.0 cm length and 7.0 cm width. Gel staining was done with ethidium bromide.
Figure 18:
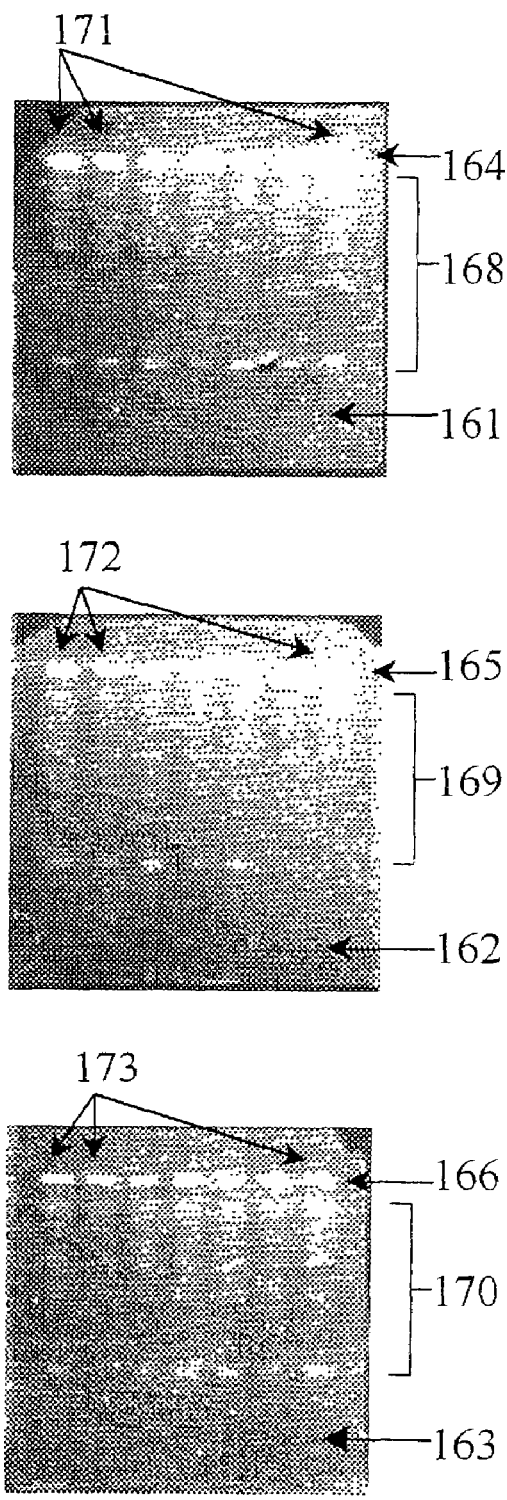
FIG. 18 shows the electrophoresis patterns obtained in three different experiments in a CHEF minichamber. In each experiment were separated the chromosomes of intact DNA samples of *Saccharomyces cerevisiae* immobilized previously in seven agarose plugs. Electrophoresis conditions: 50 s of pulse time, 3.5 hours of electrophoresis, 1 5% agarose, 0.5×TBE, 20° C., 9.82 V/cm. The square gel of 4.0 cm length was used. Gel staining was done with ethidium bromide.

Chambers for pulsed field electrophoresis, methods and accessories disclosed in this invention have the following advantages:

1—Chambers saving laboratory bench space and chemical and biological reagents are provided. That is, they use a small amount of buffer solution and biological sample
2—A method for constructing CHEF and TAFE minichambers, casting the gels and calculating the volume of buffer solution to be used is provided. The method only needs to be fed with the separation between the electrodes with opposite polarity
3—Although the buffer circulates throughout the chambers at high flow velocity and the chambers are filled with a small buffer volume, the band patterns are reproducible, because a system is provided for attenuating turbulences of the buffer solution flowing throughout the chambers.
4—The chambers are small, thus, high electric fields can be applied using power supplies of low power output, so the electrophoresis is performed in short times As a rule, the electrophoresis times to separate molecules up to 2 megabase pairs are near to 8 hours.
5—The accessories, for casting gels and loading the sample plugs into the wells, permit to cast gels of flat surfaces and to align the loaded sample plugs lengthwise the migration origin. This and the circulation of the solution at high flow velocity with the attenuation of the turbulences of the fluid contribute to obtain reproducible straight band patterns.
6—The system for pulling tight the electrodes avoids the slackening of the electrodes, thus avoiding distortions of the electric field force lines and, then, contributing to the reproducibility of the band patterns.
7—The system for pulling tight the electrodes facilitates that the electrodes of TAFE chambers can be pulled tight by the experimenter when they are slackened. The system for pulling tight electrodes also has associated a system of elastic plugs that seal the holes through which the electrodes are passed, preventing the buffer solution from leaking even if the electrode diameter reduces due to wear.
8—An accessory set for the preparation of thin sample plugs having dimensions matching with the gel wells is provided.
9—The system used to place the electrodes in the chamber permits to save platinum wire. As the chambers are small, other materials used are also saved, lowering costs
10—A method is provided to determine the electrophoresis run times for different experimental conditions. The method is based on equations that describe the migration of DNA molecules in CHEF chambers under pulsed field gel electrophoresis.
11—The gels used by minichambers are large enough to give well-resolved band patterns., thus they are useful in analytical and preparative applications. They are also wide enough to allow to be loaded with numerous samples in a single experiment
12—The chambers support numerous UEZ, which can be activated or occluded, as the experiment requires. Either type I or type II TAFE chambers can have several UEZ, therefore they accommodate one or several minigels and can analyze few or many samples. The maximum number of samples 'Nt' that can be analyzed in an electrophoresis is a multiple of the number of UEZ.
13—The co-electrophoresis of few or many samples is done in short time. Either type I or type II TAFE chambers can separate quickly the DNA molecules contained in several samples. For example, when using four minigels, 80 seconds of pulse duration, 8 33 V/cm and 15° C., only 12 hours are required to separate the *Saccharomyces cerevisiae* chromosomes.
14—The amount of reagents needed by type I and type II TAFE chambers depends on the number of samples to be analyzed, and thus, on the number of UEZ activated ('Nzue'). It holds that the volume of buffer filling the chamber is Bc=Nzue·Bnt.
15—Equations that permit to design optimally the dimensions of TAFE chambers as well as to select the maximum values of the electric field that can be applied in them are provided. The maximum electric field that can be applied depends on the length of the electrodes in type I TAFE chambers and on the number of miniplatforms that will be activated in the type II TAFE chambers, provided the rest of parameters of the equations are kept constant and the power supply is properly selected.
16—Type I and type II TAFE chambers can use a little amount of buffer solution because from them can be eliminated the NEZ, regions crossed by electric field force lines that do not act on the movement of molecules.

17—The chambers having the electrodes arranged in inverted TAFE configuration are simple to construct and facilitate the manipulation of minigels during the experiments 18—The minigels of type I and type II TAFE chambers use thin samples, thus saving biological reagents and reducing the electrophoresis run time.

19—Chambers with multiple UEZ are useful to perform molecular epidemiology studies, to analyze strain collections, to analyze YAC and BAC clones, and to perform any other application involving a large number of samples

The invention claimed is:

1. Pulsed field electrophoresis chambers with Transversal Alternating Field Electrophoresis (TAFE) electrode array having two pairs of electrodes, each pair formed by one cathode and one anode, for separating DNA molecules immobilized in agarose plugs loaded into a vertical gel by means of using a system for energizing the electrodes and alternating the direction of application of an electric field crossing the gel transversally and generated by the electrode array, as well as a system for circulating a buffer solution throughout the chamber, which TAFE chambers comprise:

i) one or more minigels placed in zones crossed by lines of force of the electric field interacting directly with DNA molecules loaded into said minigel(s), wherein said zones are Useful Electrophoresis Zones (UEZ) of said TAFE chambers, ii) said pairs of electrodes of opposite polarities, cathode and anode, separated in the TAFE electrode array a distance 'd', which is from 6.2 to 15 cm; wherein said distance in conjunction with the number and sizes of said UEZs limit to certain values height, depth and width of said TAFE chambers, length and width of said minigel(s), and total number of samples loaded simultaneously into all said minigel(s), iii) blocks of materials of high dielectric constant occluding zones of said TAFE chambers crossed by the electric field force lines not acting on DNA molecules loaded into said minigel(s), wherein said zones are non-useful electrophoresis zones (NEZ) zones of said TAFE chambers, iv) stretched electrodes, fixed and pulled tight by the action of a fixation and a tension system, v) inverted TAFE electrode configuration in said electrode array, and vi) three accessory sets of said TAFE chambers for homogenizing the electric current flowing through said chambers in the electrophoresis; the first set comprising removable sheets that avoid turbulences of buffer circulated at high flow velocity; the second set comprising disassemblable sets of frames, base plates, covers and combs having teeth for casting said minigels with homogeneous cross sectional area and identical wells; and the third set comprising disassemblable systems of grooved blocks or sample plug makers, covers of said grooved blocks, and cutters for preparing DNA samples immobilized in plugs for said minigels.

2. Electrophoresis chambers of claim 1 wherein each electrode of said electrode array is parallel to a frontal wall of each TAFE chamber and has a length ('L') of up to 50 cm wherein L is equal to the width of said chamber.

3. Electrophoresis chambers of claim 1 wherein said minigels are d·0.515 cm in length and said length is from 3.2 to 7.7 cm.

4. Electrophoresis chambers of claim 1 wherein said minigels are from 1.7 to 50 cm in width and have a number 'NM' of wells supporting 'NM' number of DNA sample plugs, wherein said 'NM' is equal to (said minigel width in cm −0.2)/0.25.

5. Electrophoresis chambers of claim 1 wherein said distance 'd' limits height and depth of said TAFE chambers by limiting to $[2+1.4·d]·[2+0.54·d]-1.02·[1+0.54·d]^2$ cm$^2$ the area of a chamber lateral wall, or wall supporting the electrodes and the minigels, wherein said area is from 37.8 to 147.8 cm$^2$.

6. Electrophoresis chambers of claim 1 wherein said TAFE chambers are evenly subdivided into several UEZs with one minigel in each UEZ, wherein the number of UEZs is from 1 to 30.

7. Electrophoresis chambers of claim 6 wherein said UEZs are as wide as each minigel and are fully occluded with rectangular blocks made of materials with high dielectric constant.

8. Electrophoresis chambers of claim 1 wherein said minigels are arranged sequentially one next to the other, with their faces parallel to the electrodes.

9. Electrophoresis chambers of claim 1 wherein the electrode array of one of said TAFE chambers is in a fixed or removable single electrode platform (type I TAFE chamber), wherein each electrode of said electrode array is up to 50 cm in length.

10. The electrophoresis chamber of claim 9 wherein said single electrode platform of said type I TAFE chamber is evenly subdivided and forms several UEZs with all minigels supported in a single frame.

11. The electrophoresis chamber of claim 9 wherein said single electrode platform of said type I TAFE chamber is evenly subdivided and forms several UEZs with each minigel independently placed in each UEZ, wherein said minigels slide through laterally grooved pieces of said TAFE chambers.

12. Electrophoresis chambers of claim 1 wherein said electrodes of one of said TAFE chambers are in various fixed or removable independent mini-platforms, wherein each mini-platform limits one useful electrophoresis zone (UEZ), has one minigel, and bears its electrodes physically separated from the electrodes of the remaining mini-platforms (type II TAFE chamber); wherein said physically separated electrodes of one mini-platform acquire continuity with the electrodes of said remaining mini-platforms by plugging them in parallel, such that said TAFE chamber is energized with a single power supply and samples loaded into the minigels of the mini-platforms are exposed to the same electrophoresis conditions.

13. Electrophoresis chambers of claim 1 wherein said inverted TAFE electrode configuration comprises the cathodes of the electrode array being disposed at the bottom of the electrophoresis chamber and the anodes at the top, so samples are loaded into the minigel bottom and migrate in the direction opposite to the gravity.

14. Electrophoresis chambers of claim 1 wherein one of said blocks occluding NEZ of said TAFE chambers has its outer side parallel to the frontal wall of said TAFE chambers and its inner side forms a small angle with a plane containing one of said cathodes and one of said anodes located at the same side of the minigel(s).

15. Electrophoresis chambers of claim 1 wherein said stretched electrodes are fixed to said TAFE chambers by the action of the fixation system, wherein said system comprises bored elastic plugs inserted into holes drilled into lateral walls of said chambers, and said electrodes enter into said TAFE chambers from the outside passing through the bores of said elastic plugs.

16. Electrophoresis chambers of claim 15 wherein said elastic plugs are made of silicone or rubber.

17. Electrophoresis chambers of claim 1 wherein said system for pulling tight each electrode of said TAFE chambers comprises
　i) a slotted rod with a hole crossing a waist-shaped notch, wherein said slotted rod bears the slot in its top side,
　ii) said electrode inserted into said hole, bent and wrapped around said waist-shaped notch,
　iii) a grub screw for immobilizing or releasing said slotted rod in desired position,
wherein said slotted rod is located at the electrode exit of said TAFE chamber.

18. Electrophoresis chambers of claim 1 wherein said first set comprises two removable and identical sheets made of a material with high dielectric constant, wherein each sheet is the size of the chamber wall parallel to the electrodes and bears a horizontal slot in its lower third, wherein said slot is 0.3 cm in height and as long as each electrode.

19. Electrophoresis chambers of claim 18 wherein the two identical sheets are placed as follows: one of said sheets near to the buffer inlet and the other near to the outlet, and said sheets divide said TAFE chambers in three compartments: a central compartment containing the electrodes and the minigels, and two lateral compartments for delivering buffer solution into the chambers or withdrawing said buffer solution from them.

20. Electrophoresis chambers of claim 1 wherein the second set of said TAFE chambers comprises:
　i) a flat base plate,
　ii) two frames with two lateral notches for inserting the combs, wherein said frames are from 0.35 to 0.5 cm in thickness and have rectangular or square shaped cavities determining the shape, thickness ('th'), length and width ('a') of each minigel cast in one of said frames,
　iii) a first comb, or comb with long teeth,
　iv) two covers: the first cover fitting against the front of said first comb, and the second cover fitting against the back of said first comb,
　v) a second comb, similar to said first comb, but with shorter teeth for pushing and aligning samples loaded into said minigels.

21. Electrophoresis chambers of claim 20 wherein said first comb is flat in its frontal part, and thicker over the teeth, forming a step in the rear, wherein said teeth are identical and from 0.03 to 0.1 cm thick, from 0.15 cm to (a−0.3) cm in width, and (th−0.1) cm in length.

22. Electrophoresis chambers of claim 20 wherein said second comb has shape and sizes similar to said first comb, excepting the length of the teeth, which are 0.2 cm shorter.

23. Electrophoresis chambers of claim 20 wherein the second cover has two flat surfaces and a protruding edge; and the first cover has two flat surfaces, but one of its edges has a bevel cut in wedge formation.

24. Electrophoresis chambers of claim 1 wherein the third set of said TAFE chambers, for preparing said DNA samples immobilized in plugs for minigels, comprises:
　i) various sample plug makers, wherein each sample plug maker is a flat impermeable block thicker than 0.5 cm with multiple parallel grooves lengthwise, wherein each groove is 0.2 cm in width and from 0.03 to 0.1 cm in depth, and said depth matches the thickness of teeth of a given comb of said second set,
　ii) a flat rigid and impermeable sheet of at least 0.1 cm in thickness, wich is a cover of said sample plug maker,
　iii) sample plug cutters, wherein each cutter is a bar as long as, or longer than the grooves of one of said sample plug makers, and said bar bears several protuberances with cutting edges in its inferior part and protruding 0.1 cm from the bar, wherein said cutting edges are evenly spaced, and said spacing is 0.15 cm at least.

25. Electrophoresis chambers of claim 1 wherein one of said TAFE chambers bearing a single UEZ is energized at electric field strength up to 25 V/cm using a power supply with maximum power output of 300 watt, and contains 0.5×TBE buffer solution is used and maintained at constant temperature from 4 to 30° C., wherein 1×TBE is 89 mM Tris, 89 mM boric acid and 2 mM EDTA, pH 8.3.

26. Electrophoresis chambers of claim 1 wherein one of said TAFE chambers with several UEZs is energized with a single power supply at electric field strength from 8 to 25 V/cm,and contains 0.5×TBE buffer solution maintained at constant temperature from 4 to 30° C., wherein 1×TBE is 89 mM Tris, 89 mM boric acid and 2 mM EDTA, pH 8.3.

* * * * *